US012665064B2

(12) United States Patent
Roberts et al.

(10) Patent No.: US 12,665,064 B2
(45) Date of Patent: Jun. 23, 2026

(54) AUTOMATED CROSS-FACILITY, CROSS-CONTAINER OBJECT VALIDATION

(71) Applicant: Optum, Inc., Minnetonka, MN (US)

(72) Inventors: Warren Thomas Roberts, Phoenix, AZ (US); Michael L. Mahar, Tempe, AZ (US); Anthony Hopper, Overland Park, KS (US)

(73) Assignee: Optum, Inc., Minnetonka, MN (US)

( * ) Notice: Subject to any disclaimer, the term of this patent is extended or adjusted under 35 U.S.C. 154(b) by 318 days.

(21) Appl. No.: 18/514,963

(22) Filed: Nov. 20, 2023

(65) Prior Publication Data

US 2025/0166773 A1 May 22, 2025

(51) Int. Cl.
*G16H 20/13* (2018.01)
*A61J 7/02* (2006.01)

(52) U.S. Cl.
CPC .............. *G16H 20/13* (2018.01); *A61J 7/02* (2013.01); *A61J 2200/74* (2013.01); *A61J 2205/00* (2013.01)

(58) Field of Classification Search
CPC ......... G16H 20/13; A61J 7/02; A61J 2200/74; A61J 2205/00
See application file for complete search history.

(56) References Cited

U.S. PATENT DOCUMENTS 6,232,876 B1 * 5/2001 Maloney ............ G08B 13/1427
340/568.1
6,707,381 B1 3/2004 Maloney

| | | |
|---|---|---|
| 10,029,856 B2 | 7/2018 | Greyshock |
| 10,528,911 B1 * | 1/2020 | Laster .................... G16H 20/10 |
| 10,565,544 B1 | 2/2020 | Lee et al. |
| 10,769,579 B1 | 9/2020 | Smith et al. |
| 2006/0038010 A1 | 2/2006 | Lucas |

(Continued)

FOREIGN PATENT DOCUMENTS

EP 4116901 A1 1/2023

OTHER PUBLICATIONS

Notice of Allowance and Fees Due (PTOL-85) Mailed on Mar. 20, 2026 for U.S. Appl. No. 18/515,003, 9 page(s).

*Primary Examiner* — Kyle O Logan
(74) *Attorney, Agent, or Firm* — Alston & Bird LLP

(57) ABSTRACT

Various embodiments of the present disclosure object provide tracking and monitoring techniques for implementing improved distribution systems in various environments. The techniques of the present disclosure may include receiving a transition identifier corresponding to a transitioning data object that include (a) a first object count of a plurality of transitioning objects within a transitioning container, (b) an intake identifier corresponding to the plurality of transitioning objects, and (c) a pallet identifier for a conveyor pallet configured to move the transitioning container. The techniques may include receiving a canister identifier corresponding to a distribution canister and in response to receiving the transition identifier and the canister identifier, (a) linking the canister and transition container, (b) determining, a second object count corresponding to the distribution canister, and (c) initiating a compliance operation based on a comparison between the first object count and the second object count.

20 Claims, 9 Drawing Sheets

(56)   References Cited

U.S. PATENT DOCUMENTS

| | | | |
|---|---|---|---|
| 2006/0058918 A1* | 3/2006 | Handfield | G07F 9/026 |
| | | | 700/236 |
| 2008/0128452 A1* | 6/2008 | Witczak | G07F 17/0092 |
| | | | 221/290 |
| 2008/0319577 A1 | 12/2008 | Vahlberg et al. | |
| 2008/0319790 A1 | 12/2008 | Vahlberg et al. | |
| 2011/0050424 A1* | 3/2011 | Cova | G06Q 10/0833 |
| | | | 340/572.1 |
| 2013/0018356 A1 | 1/2013 | Prince et al. | |
| 2014/0350715 A1 | 11/2014 | Gopalakrishnan et al. | |
| 2015/0042795 A1 | 2/2015 | Tsuria et al. | |
| 2015/0178673 A1 | 6/2015 | Penneman | |
| 2016/0364686 A1 | 12/2016 | Wolfe et al. | |
| 2018/0282066 A1 | 10/2018 | Wagner et al. | |
| 2022/0415466 A1* | 12/2022 | Louie | G06Q 10/087 |

* cited by examiner

COMPLIANCE DATASET 428

HISTORIC TUPLE 430

PALLET DATA OBJECT 424

TRANSITION IDENTIFIER 414

INTAKE IDENTIFIER 406

PALLET IDENTIFIER 426

CANISTER DATA OBJECT 602

TRANSITION IDENTIFIER 414

INTAKE IDENTIFIER 406

CANISTER IDENTIFIER 604

TRANSITIONING DATA OBJECT 412

TRANSITION IDENTIFIER 414

INTAKE IDENTIFIER 406

PALLET IDENTIFIER 426

FIRST OBJECT COUNT 606

COMPLIANCE OPERATION 612

WEIGHT DATA 608

INTAKE DATA OBJECT 402

TRANSITION IDENTIFIER 414

INTAKE IDENTIFIER 406

MANUFACTURING ATTRIBUTES 408

SECOND OBJECT COUNT 610

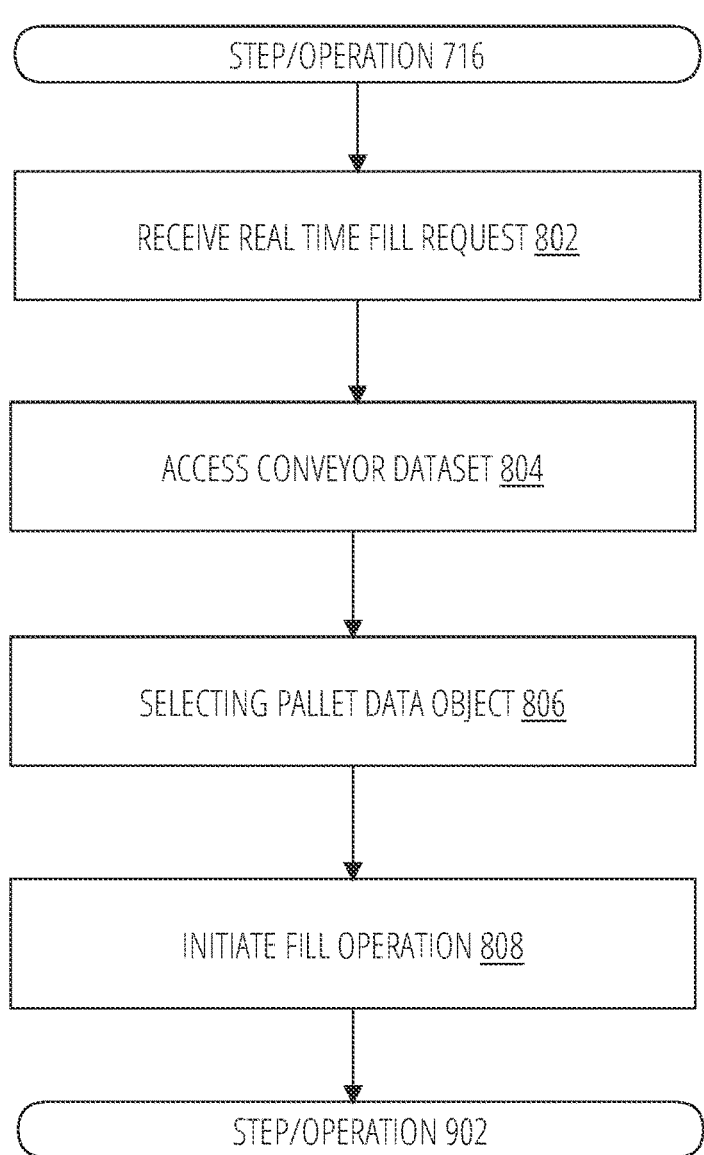
FIG. 8

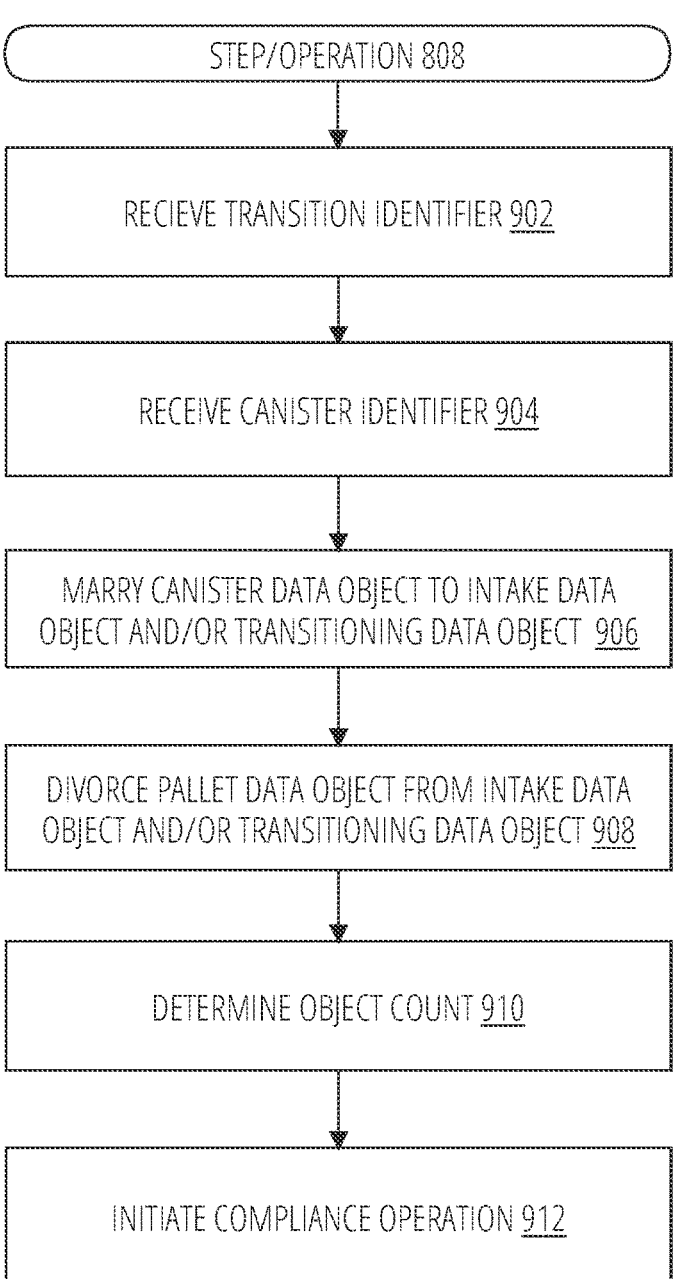
FIG. 9

AUTOMATED CROSS-FACILITY, CROSS-CONTAINER OBJECT VALIDATION

BACKGROUND

Various embodiments of the present disclosure address technical challenges related to object tracking for unique sets of small objects subject to security constraints. The techniques of the present disclosure may be applied in any of a number of different distribution environments. Traditional techniques for tracking objects rely on individual object tracking mediums, such as sensors, barcodes, and other representations that may be placed directly on an object. These techniques are incapable of tracking small objects with little surface area or other means of supporting tracking mediums. Moreover, traditional object tracking techniques are conventionally designed for a single package, and fail to account for, or monitor, the transition of objects between packages. This prevents such techniques from tracking objects across different packages that may be necessary in certain distribution environments, such as a healthcare distribution system in which tablets may be allocated from a single package to a plurality of individual, single use packages.

Various embodiments of the present disclosure make important contributions to traditional object tracking and allocation techniques by addressing these technical challenges, among others.

BRIEF SUMMARY

Various embodiments of the present disclosure provide object tracking and allocation techniques that improve traditional distribution systems by enabling comprehensive, container-to-container tracking of small objects subject to security constraints in an end-to-end distribution environment. For example, some techniques of the present disclosure enable automated object transitioning techniques that track object locations in real time to address real time object requirements within a distribution system. Unlike traditional techniques, the locations of various sets of objects may be accurately tracked across a distribution environment to optimally select an object set for satisfying real time object demands of a distribution system. As another example, some techniques of the present disclosure enable automated object verification techniques that enable the continuous investigation and evaluation of object sets as they traverse a distribution environment. This, in turn, allows for the automatic distribution of objects subject to security measures while enforcing strict compliance actions in an automated system. Each of these examples improve processing efficiencies, automation processes, and object throughput with respect to traditional distribution systems, while enabling the safe, secure, and compliant distribution of small objects subject to security measures.

In some embodiments, a computer-implemented method includes receiving, by one or more processors, a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container; receiving, by the one or more processors, a canister identifier corresponding to a distribution canister; in response to receiving the transition identifier and the canister identifier, (i) assigning, by the one or more processors, the transition identifier and the intake identifier to a canister data object corresponding to the distribution canister, (ii) assigning, by the one or more processors, the canister identifier to a target intake data object corresponding to the intake identifier, and (iii) removing, by the one or more processors, the intake identifier and the transition identifier from a pallet data object corresponding to the pallet identifier; determining, by the one or more processors, a second object count corresponding to the distribution canister; and initiating, by the one or more processors, a compliance operation based on a comparison between the first object count and the second object count.

In some embodiments, a computing system includes memory and one or more processors communicatively coupled to the memory, the one or more processors are configured to receive a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container; receive a canister identifier corresponding to a distribution canister; in response to receiving the transition identifier and the canister identifier, (i) assign the transition identifier and the intake identifier to a canister data object corresponding to the distribution canister, (ii) assign the canister identifier to a target intake data object corresponding to the intake identifier, and (iii) remove the intake identifier and the transition identifier from a pallet data object corresponding to the pallet identifier; determine a second object count corresponding to the distribution canister; and initiate a compliance operation based on a comparison between the first object count and the second object count.

In some embodiments, one or more non-transitory computer-readable storage media including instructions that, when executed by one or more processors, cause the one or more processors to receive a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container; receive a canister identifier corresponding to a distribution canister; in response to receiving the transition identifier and the canister identifier, (i) assign the transition identifier and the intake identifier to a canister data object corresponding to the distribution canister, (ii) assign the canister identifier to a target intake data object corresponding to the intake identifier, and (iii) remove the intake identifier and the transition identifier from a pallet data object corresponding to the pallet identifier; determine a second object count corresponding to the distribution canister; and initiate a compliance operation based on a comparison between the first object count and the second object count.

BRIEF DESCRIPTION OF DRAWINGS

FIG. 6 is a dataflow diagram showing example data structures and modules for an automated object verification technique in accordance with some embodiments discussed herein.

FIG. 8 is a flowchart showing an example of an automated object transitioning process in accordance with some embodiments discussed herein.

FIG. 9 is a flowchart showing an example of an automated object verification process in accordance with some embodiments discussed herein.

<div align="center">DETAILED DESCRIPTION</div>

Figure 1:
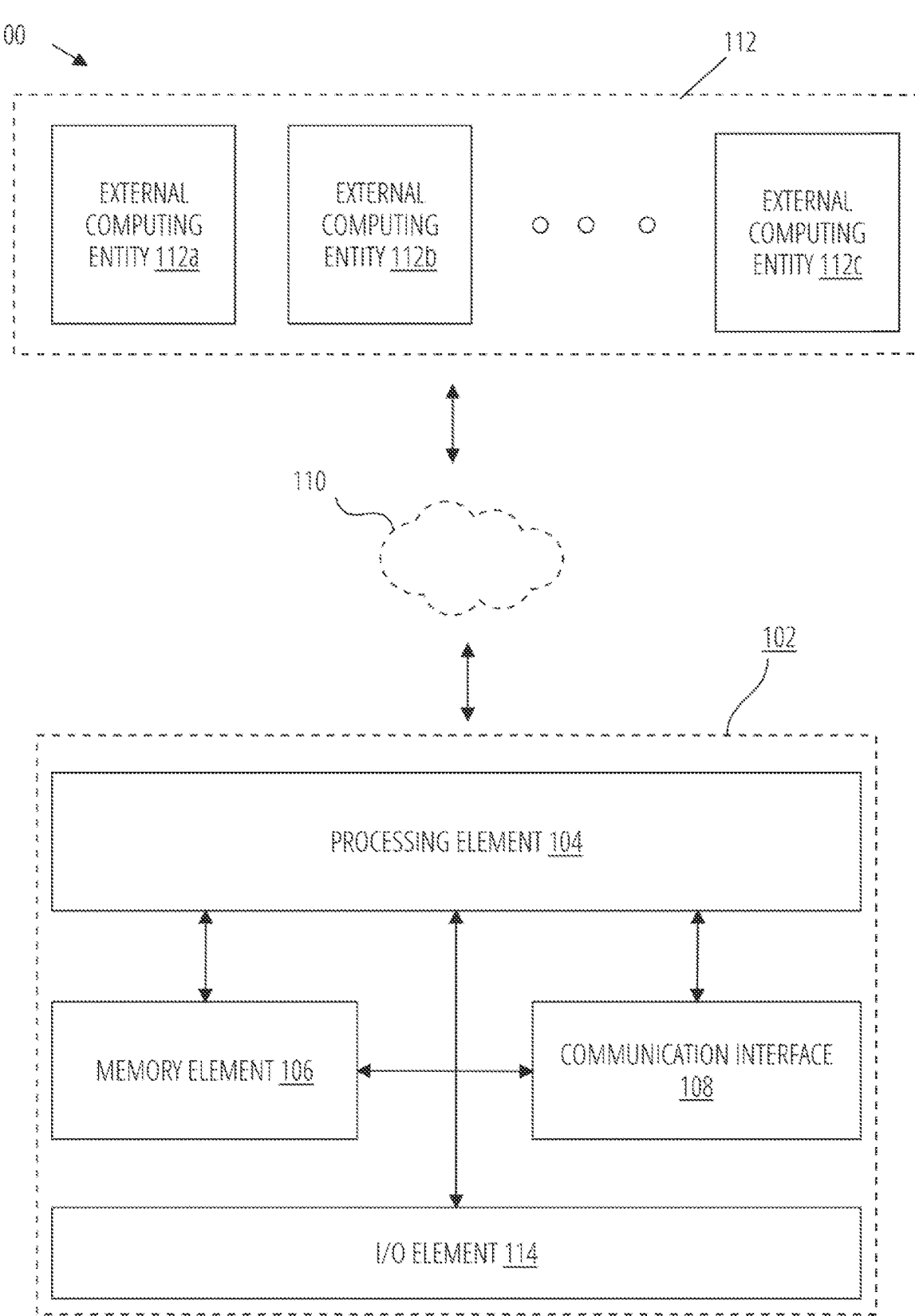
FIG. 1 illustrates an example computing system in accordance with one or more embodiments of the present disclosure.

Various embodiments of the present disclosure are described more fully hereinafter with reference to the accompanying drawings, in which some, but not all embodiments of the present disclosure are shown. Indeed, the present disclosure may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "example" are used to be examples with no indication of quality level. Terms such as "computing," "determining," "generating," and/or similar words are used herein interchangeably to refer to the creation, modification, or identification of data. Further, "based on," "based at least in part on," "based at least on," "based upon," and/or similar words are used herein interchangeably in an open-ended manner such that they do not indicate being based only on or based solely on the referenced element or elements unless so indicated. Like numbers refer to like elements throughout. Moreover, while certain embodiments of the present disclosure are described with reference to predictive data analysis, one of ordinary skills in the art will recognize that the disclosed concepts may be used to perform other types of data analysis.

<div align="center">I. COMPUTER PROGRAM PRODUCTS,
METHODS, AND COMPUTING ENTITIES</div>

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together, such as in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In some embodiments, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like). A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In some embodiments, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for, or used in addition to, the computer-readable storage media described above.

As should be appreciated, various embodiments of the present disclosure may also be implemented as methods, apparatuses, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises a combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some example embodiments, retrieval, loading, and/or execution may be performed in parallel such that multiple instructions are retrieved, loaded, and/or executed together. Thus, such embodiments may produce specifically configured machines performing the steps or operations specified in the block diagrams and flowchart illustrations. Accordingly, the block diagrams and flowchart illustrations support various combinations of embodiments for performing the specified instructions, operations, or steps.

II. EXAMPLE FRAMEWORK

FIG. 1 illustrates an example computing system 100 in accordance with one or more embodiments of the present disclosure. The computing system 100 may include a predictive computing entity 102 and/or one or more external computing entities 112a-c communicatively coupled to the predictive computing entity 102 using one or more wired and/or wireless communication techniques. The predictive computing entity 102 may be specially configured to perform one or more steps/operations of one or more techniques described herein. In some embodiments, the predictive computing entity 102 may include and/or be in association with one or more mobile device(s), desktop computer(s), laptop (s), server(s), cloud computing platform(s), and/or the like. In some example embodiments, the predictive computing entity 102 may be configured to receive and/or transmit one or more datasets, objects, and/or the like from and/or to the external computing entities 112a-c to perform one or more steps/operations of one or more techniques (e.g., tracking techniques, monitoring techniques, visualization techniques, compliance techniques, distribution techniques, and/or the like) described herein.

The external computing entities 112a-c, for example, may include and/or be associated with one or more entities that may be configured to receive, store, manage, and/or facilitate datasets, such as conveyor datasets, compliance datasets, order datasets, and/or the like. The external computing entities 112a-c may provide such datasets, and/or the like to the predictive computing entity 102 which may leverage the datasets to generate tracking insights for small objects within an distribution environment. In some examples, the datasets may include an aggregation of data from across the external computing entities 112a-c into one or more aggregated datasets. The external computing entities 112a-c, for example, may be associated with one or more data repositories, cloud platforms, compute nodes, organizations, and/or the like, which may be individually and/or collectively leveraged by the predictive computing entity 102 to obtain and aggregate data for a prediction domain.

The predictive computing entity 102 may include, or be in communication with, one or more processing elements 104 (also referred to as processors, processing circuitry, digital circuitry, and/or similar terms used herein interchangeably) that communicate with other elements within the predictive computing entity 102 via a bus, for example. As will be understood, the predictive computing entity 102 may be embodied in a number of different ways. The predictive computing entity 102 may be configured for a particular use or configured to execute instructions stored in volatile or non-volatile media or otherwise accessible to the processing element 104. As such, whether configured by hardware or computer program products, or by a combination thereof, the processing element 104 may be capable of performing steps or operations according to embodiments of the present disclosure when configured accordingly.

In one embodiment, the predictive computing entity 102 may further include, or be in communication with, one or more memory elements 106. The memory element 106 may be used to store at least portions of the databases, database instances, database management systems, data, applications, programs, program modules, scripts, source code, object code, byte code, compiled code, interpreted code, machine code, executable instructions, and/or the like being executed by, for example, the processing element 104. Thus, the databases, database instances, database management systems, data, applications, programs, program modules, scripts, source code, object code, byte code, compiled code, interpreted code, machine code, executable instructions, and/or the like, may be used to control certain aspects of the operation of the predictive computing entity 102 with the assistance of the processing element 104.

As indicated, in one embodiment, the predictive computing entity 102 may also include one or more communication interfaces 108 for communicating with various computing entities, e.g., external computing entities 112a-c, such as by communicating data, content, information, and/or similar terms used herein interchangeably that may be transmitted, received, operated on, processed, displayed, stored, and/or the like.

The computing system 100 may include one or more input/output (I/O) element(s) 114 for communicating with one or more users. An I/O element 114, for example, may include one or more user interfaces for providing and/or receiving information from one or more users of the computing system 100. The I/O element 114 may include one or more tactile interfaces (e.g., keypads, touch screens, etc.), one or more audio interfaces (e.g., microphones, speakers, etc.), visual interfaces (e.g., display devices, etc.), and/or the like. The I/O element 114 may be configured to receive user input through one or more of the user interfaces from a user of the computing system 100 and provide data to a user through the user interfaces.

Figure 2:
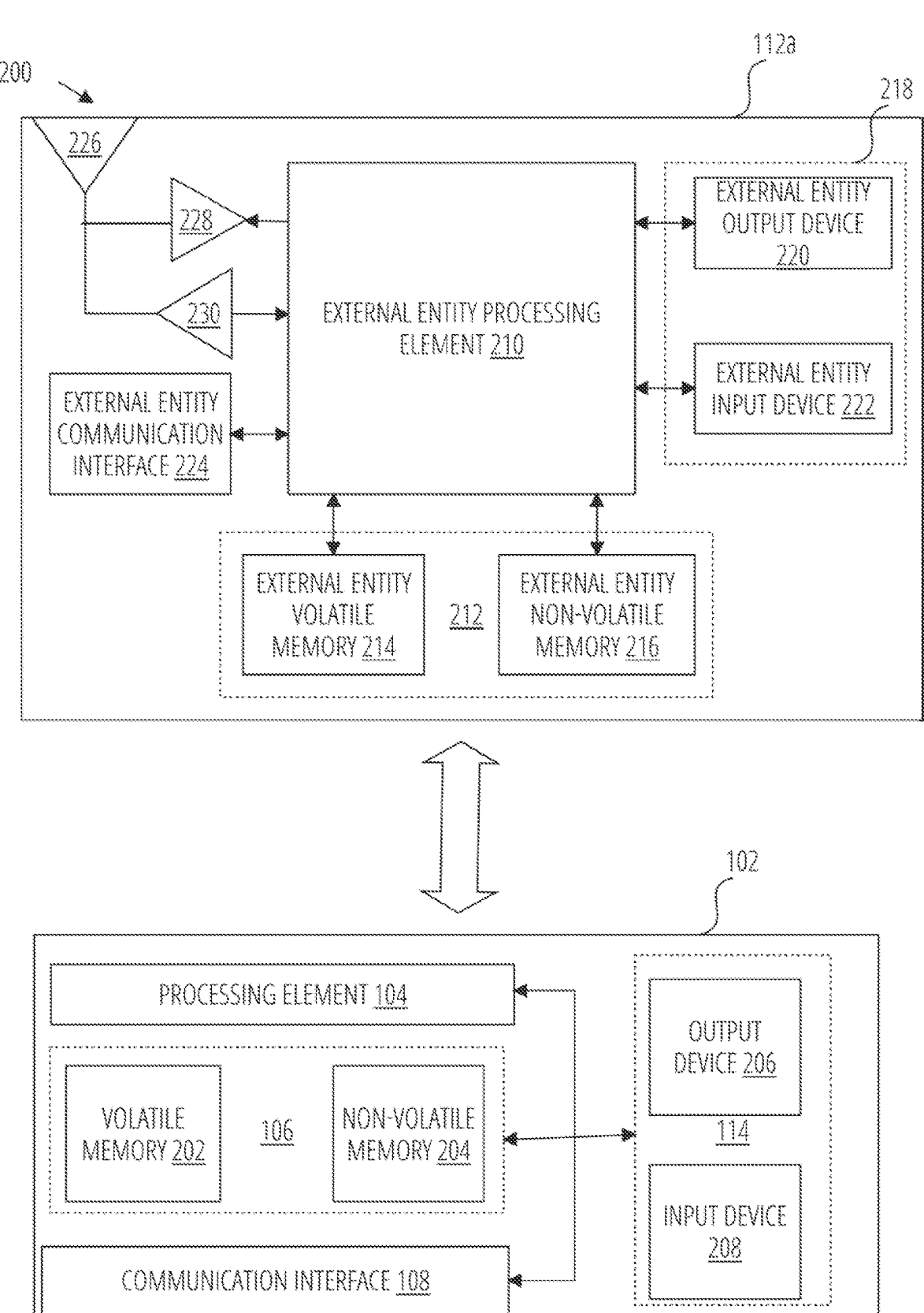
FIG. 2 is a schematic diagram showing a system computing architecture in accordance with one or more embodiments of the present disclosure.

FIG. 2 is a schematic diagram showing a system computing architecture 200 in accordance with some embodiments discussed herein. In some embodiments, the system computing architecture 200 may include the predictive computing entity 102 and/or the external computing entity 112*a* of the computing system 100. The predictive computing entity 102 and/or the external computing entity 112*a* may include a computing apparatus, a computing device, and/or any form of computing entity configured to execute instructions stored on a computer-readable storage medium to perform certain steps or operations.

The predictive computing entity 102 may include a processing element 104, a memory element 106, a communication interface 108, and/or one or more I/O elements 114 that communicate within the predictive computing entity 102 via internal communication circuitry, such as a communication bus, and/or the like.

The processing element 104 may be embodied as one or more complex programmable logic devices (CPLDs), microprocessors, multi-core processors, coprocessing entities, application-specific instruction-set processors (ASIPs), microcontrollers, and/or controllers. Further, the processing element 104 may be embodied as one or more other processing devices or circuitry including, for example, a processor, one or more processors, various processing devices, and/or the like. The term circuitry may refer to an entirely hardware embodiment or a combination of hardware and computer program products. Thus, the processing element 104 may be embodied as integrated circuits, application specific integrated circuits (ASICs), field programmable gate arrays (FPGAs), programmable logic arrays (PLAs), hardware accelerators, digital circuitry, and/or the like.

The memory element 106 may include volatile memory 202 and/or non-volatile memory 204. The memory element 106, for example, may include volatile memory 202 (also referred to as volatile storage media, memory storage, memory circuitry, and/or similar terms used herein interchangeably). In one embodiment, a volatile memory 202 may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for, or used in addition to, the computer-readable storage media described above.

The memory element 106 may include non-volatile memory 204 (also referred to as non-volatile storage, memory, memory storage, memory circuitry, and/or similar terms used herein interchangeably). In one embodiment, the non-volatile memory 204 may include one or more non-volatile storage or memory media, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

In one embodiment, a non-volatile memory 204 may include a floppy disk, flexible disk, hard disk, solid-state storage (SSS) (e.g., a solid-state drive (SSD)), solid state card (SSC), solid state module (SSM), enterprise flash drive, magnetic tape, or any other non-transitory magnetic medium, and/or the like. A non-volatile memory 204 may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile memory 204 may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

As will be recognized, the non-volatile memory 204 may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

The memory element 106 may include a non-transitory computer-readable storage medium for implementing one or more aspects of the present disclosure including as a computer-implemented method configured to perform one or more steps/operations described herein. For example, the non-transitory computer-readable storage medium may include instructions that when executed by a computer (e.g., processing element 104), cause the computer to perform one or more steps/operations of the present disclosure. For instance, the memory element 106 may store instructions that, when executed by the processing element 104, configure the predictive computing entity 102 to perform one or more steps/operations described herein.

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language, such as an assembly language associated with a particular hardware framework and/or operating system platform. A software component comprising assembly language instructions may require conversion into executable machine code by an assembler prior to execution by the hardware framework and/or platform. Another example programming language may be a higher-level programming language that may be portable across multiple frameworks. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together, such as in a particular directory, folder, or library. Software components may be static (e.g., pre-established, or fixed) or dynamic (e.g., created or modified at the time of execution).

The predictive computing entity 102 may be embodied by a computer program product which includes non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media such as the volatile memory 202 and/or the non-volatile memory 204.

The predictive computing entity 102 may include one or more I/O elements 114. The I/O elements 114 may include one or more output devices 206 and/or one or more input devices 208 for providing and/or receiving information with a user, respectively. The output devices 206 may include one or more sensory output devices, such as one or more tactile output devices (e.g., vibration devices such as direct current motors, and/or the like), one or more visual output devices (e.g., liquid crystal displays, and/or the like), one or more audio output devices (e.g., speakers, and/or the like), and/or the like. The input devices 208 may include one or more sensory input devices, such as one or more tactile input devices (e.g., touch sensitive displays, push buttons, and/or the like), one or more audio input devices (e.g., microphones, and/or the like), and/or the like.

In addition, or alternatively, the predictive computing entity 102 may communicate, via a communication interface 108, with one or more external computing entities such as the external computing entity 112a. The communication interface 108 may be compatible with one or more wired and/or wireless communication protocols.

For example, such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. In addition, or alternatively, the predictive computing entity 102 may be configured to communicate via wireless external communication using any of a variety of protocols, such as general packet radio service (GPRS), Universal Mobile Telecommunications System (UMTS), Code Division Multiple Access 2000 (CDMA2000), CDMA2000 1x (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.9 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

The external computing entity 112a may include an external entity processing element 210, an external entity memory element 212, an external entity communication interface 224, and/or one or more external entity I/O elements 218 that communicate within the external computing entity 112a via internal communication circuitry, such as a communication bus and/or the like.

The external entity processing element 210 may include one or more processing devices, processors, and/or any other device, circuitry, and/or the like described with reference to the processing element 104. The external entity memory element 212 may include one or more memory devices, media, and/or the like described with reference to the memory element 106. The external entity memory element 212, for example, may include at least one external entity volatile memory 214 and/or external entity non-volatile memory 216. The external entity communication interface 224 may include one or more wired and/or wireless communication interfaces as described with reference to communication interface 108.

In some embodiments, the external entity communication interface 224 may be supported by one or more radio circuitry. For instance, the external computing entity 112a may include an antenna 226, a transmitter 228 (e.g., radio), and/or a receiver 230 (e.g., radio).

Signals provided to and received from the transmitter 228 and the receiver 230, correspondingly, may include signaling information/data in accordance with air interface standards of applicable wireless systems. In this regard, the external computing entity 112a may be capable of operating with one or more air interface standards, communication protocols, modulation types, and access types. More particularly, the external computing entity 112a may operate in accordance with any of a number of wireless communication standards and protocols, such as those described above with regard to the predictive computing entity 102.

Via these communication standards and protocols, the external computing entity 112*a* may communicate with various other entities using means such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 112*a* may also download changes, add-ons, and updates, for instance, to its firmware, software (e.g., including executable instructions, applications, program modules), operating system, and/or the like.

According to one embodiment, the external computing entity 112*a* may include location determining embodiments, devices, modules, functionalities, and/or the like. For example, the external computing entity 112*a* may include outdoor positioning embodiments, such as a location module adapted to acquire, for example, latitude, longitude, altitude, geocode, course, direction, heading, speed, universal time (UTC), date, and/or various other information/data. In one embodiment, the location module may acquire data, such as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data may be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data may be determined by triangulating a position of the external computing entity 112*a* in connection with a variety of other systems, including cellular towers, Wi-Fi access points, and/or the like. Similarly, the external computing entity 112*a* may include indoor positioning embodiments, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops), and/or the like. For instance, such technologies may include the iBeacons, Gimbal proximity beacons, Bluetooth Low Energy (BLE) transmitters, NFC transmitters, and/or the like. These indoor positioning embodiments may be used in a variety of settings to determine the location of someone or something with inches or centimeters.

The external entity I/O elements 218 may include one or more external entity output devices 220 and/or one or more external entity input devices 222 that may include one or more sensory devices described herein with reference to the I/O elements 114. In some embodiments, the external entity I/O element 218 may include a user interface (e.g., a display, speaker, and/or the like) and/or a user input interface (e.g., keypad, touch screen, microphone, and/or the like) that may be coupled to the external entity processing element 210.

For example, the user interface may be a user application, browser, and/or similar words used herein interchangeably executing on and/or accessible via the external computing entity 112*a* to interact with and/or cause the display, announcement, and/or the like of information/data to a user. The user input interface may include any of a number of input devices or interfaces allowing the external computing entity 112*a* to receive data including, as examples, a keypad (hard or soft), a touch display, voice/speech interfaces, motion interfaces, and/or any other input device. In embodiments including a keypad, the keypad may include (or cause display of) the conventional numeric (0-9) and related keys (#, *, and/or the like), and other keys used for operating the external computing entity 112*a* and may include a full set of alphabetic keys or set of keys that may be activated to provide a full set of alphanumeric keys. In addition to providing input, the user input interface may be used, for example, to activate or deactivate certain functions, such as screen savers, sleep modes, and/or the like.

III. EXAMPLES OF CERTAIN TERMS

In some embodiments, the term "distribution object" refers to a physical entity that is processed by a distribution system. A distribution object may include any type of object that may be received, processed, and then dispatched by a distribution system to resolve an order. The type of distribution object may depend on the distribution system. As one example, for a healthcare distribution system, a distribution object may include a form of medication, such as a tablet, capsule, and/or the like, that may hold a particular dosage of elements prescribed for a member of a healthcare system. In such a case, the distribution object may be subject to strict regulations and security measures for ensuring that the correct object is provided to a correct member. At the same time, the distribution object may be limited in size, such that traditional forms of object tracking are unavailable to comply with the strict regulatory and security measures. Some of the techniques of the present disclosure may improve the distribution operations of traditional distribution system to accommodate for unique characteristics, such as size and security constraints, of distribution objects, such as those used in healthcare systems.

In some embodiments, the term "object identifier" refers to a data value (e.g., sequence of numeric, alpha-numeric characters, etc.) that identifies a distribution object and/or type of distribution object. An object identifier, for example, may include a stock keeping unit (SKU), serial number, and/or the like for uniquely identifying a distribution object. The object identifier may depend on the type of distribution object. For instance, in a healthcare system with regulated objects, an object identifier may be a code, tag, and/or the like that is assigned by a regulatory body. By way of example, an object identifier may include a National Drug Code (NDC) for a medication.

In some embodiments, the term "intake object" refers to a distribution object at intake to a distribution system. An intake object, for example, may refer to a distribution object at the first phase, such as a portion of a bulk-up phase, of a distribution process. In some examples, an intake object may include one of a plurality of intake objects that are grouped into an object set to begin the distribution process. The object set (e.g., an object lot), for example, may include a plurality of distribution objects aggregated from a plurality of different originating containers, such as a manufacturer's container. The object set, for example, may be created at an initial phase of a distribution process to distribute objects traditionally distributed in bulk at a granular, multi-dose level. By way of example, in a healthcare distribution system, an intake object may include an individual tablet from a tablet lot that includes a plurality of tablets aggregated from a plurality of manufacturer object containers to redistribute the tablets into single, multi-dose packages, such as pouches, for at-home delivery and consumption.

In some embodiments, the term "intake data object" refers to a data entity corresponding to a plurality of intake objects. An intake data object, for example, may include a data structure representing one or more aspects of a plurality of intake objects, such as a tablet lot aggregated from a plurality of different manufacturer object containers as described herein with respect to a healthcare distribution system.

In some embodiments, an intake data object includes a plurality of intake attributes associated with a plurality of intake objects. For instance, a plurality of intake attributes may initially include an intake identifier and/or an object identifier corresponding to the plurality of intake objects. In addition, or alternatively, an intake data object may include a plurality of manufacturing attributes that describe one or more characteristics at least partially shared by the plurality of intake objects. Each of the manufacturing attributes, for example, may be derived from a respective manufacturing object container from which the plurality of intake objects is sourced.

As described herein, an intake data object may be modified throughout a distribution process to track the plurality of intake objects and/or portions thereof as they traverse a distribution system. By way of example, an intake data object may be augmented with one or more location and/or container-based identifiers that respectively identify a physical location at and/or within which at least one intake object of the plurality of intake objects is positioned, disposed, placed, and/or the like. In this manner, using some of the techniques of the present disclosure, small, untraceable, distribution objects, such as medications, and/or the like, may be tracked through chains of identifiers stored within the intake data object.

In some embodiments, the term "intake identifier" refers to a data value (e.g., sequence of numeric, alpha-numeric characters, etc.) that identifies an intake data object. For example, the intake identifier may be an attribute of the intake data object that identifies the intake data object and/or the intake objects represented by the intake data object. An intake identifier, for example, may include a unique sequence of characters that are generated (e.g., randomly, in accordance with one or more constraints, etc.) to identify an intake data object.

In some embodiments, the term "manufacturing attributes" refers to an attribute associated with an intake object. For example, a manufacturing attribute may define one or more characteristics of an intake object that are determined from a producer and/or originator of the intake object. By way of example, a manufacturing attribute may be extracted from a manufacturer object container during an intake process of the intake object.

A manufacturing attribute may include any type of object characteristic depending on the intake object and/or distribution system. As an example, for a healthcare distribution system, a manufacturing attribute may include one or more medication attributes, such as an expiration date, usage instructions, usage caution statements, physical drug description, dosage description, pharmaceutical manufacturer, and/or the like. In some examples, a manufacturing attribute may be extracted from a manufacturer object container, such as a bulk drug container.

In some embodiments, the term "manufacturer object container" refers to a physical container from which at least a portion of a plurality of intake objects may be received. For example, a manufacturer object container may include a bottle, vial, package, intermediate bulk container, drum, insulated and/or refrigerated container, and/or the like. In some examples, a manufacturer object container may be received and/or processed (e.g., during a preparation phase) at a distribution system to generate a plurality of intake objects for allocation across a plurality of orders. A manufacturer object container may be received from an originating entity, such a manufacturer of the intake objects, an intermediary distribution entity, and/or the like.

In some embodiments, a manufacturer object container includes an identifier representation. An identifier representation, for example, may include a scannable indicium that is attached, disposed, affixed, and/or the like to an exterior surface of the manufacturer object container. In some examples, one or more manufacturing attributes of an intake data object may be identified based on scanned indicia data generated by scanning the scannable indicium with a scanning device. In some examples, an intake data object is generated in response to receiving scanned indicia data from one or more manufacturing object containers.

In some embodiments, the term "scannable indicium" to refers to a physical representation of one or more computer readable media. A scannable indicium, for example, may include a quick response (QR) code, a bar code, and/or the like. In addition, or alternatively, a scannable indicium may include a radio frequency signal, such as one or more radio frequency identifier (RFID) signals emitted by one or more active and/or passive RFID tags (e.g., transponders, etc.), near field communication (NFC) signals emitted by one or more active and/or passive NFC tags, and/or the like.

In some embodiments, the term "scanned indicia data" to refers to encoded and/or unencoded data that is generated responsive to one or more scanning operations for a scannable indicium. By way of example, scanned indicia data may include an encoded and/or unencoded identifier that is reflective of a barcode, QR code, RFID, and/or the like. In addition, or alternatively, scanned indicia data may include one or more contextual attributes corresponding to the scanned indicium. The contextual attributes, for example, may be generated, received, and/or the like, using a lookup table and/or one or more other data structure based on an encoded and/or unencoded identifier extracted from a scannable indicium.

In some embodiments, the term "scanning operation" to refers to a computing-based task configured to generate scanned indicia data. For example, a scanning operation may include the use of a scanning device to extract an encoded and/or unencoded identifier from a scannable indicium. In addition, or alternatively, a scanning operation may include one or more data collection operations for receiving contextual attributes corresponding to an encoded and/or unencoded identifier.

In some embodiments, the term "scanning device" to refers to a computing device with one or more hardware and/or software components collectively configured to generate scanned indicia data from a scannable indicum. A scanning device, for example, may include an imaging scanner, a radio frequency reader, and/or the like. A scanning device may include one or more contact and/or non-contact scanners.

In some examples, a scanning device may include an imaging scanner that includes one or more image capturing devices (e.g., cameras, etc.), lighting devices (e.g., infrared lasers, etc.), and/or the like, collectively configured to generate an image of a scannable indicium and extract scanned indicia data from the image. By way of example, an imaging scanner may include barcode and/or QR code scanners, such as a laser scanner, pen wand, charge-coupled device (CCD) scanner, and/or the like.

In addition, or alternatively, a scanning device may include a radio frequency scanner that includes one or more radio frequency receivers, transponders, and/or the like that are collectively configured to detect a radio frequency signal from a scannable indicium and extract scanned indicia data from the radio frequency signal. A radio frequency scanner, for example, may include a radio frequency readers config- ured to trigger, detect, and/or receive one or more radio frequency waves across one or more different wave lengths (e.g., low frequency bands, high frequency bands, etc.). By way of example, a radio frequency scanner may include one or more low frequency, high frequency, ultra-high fre- quency, and/or the like RFID readers, NFC readers, and/or any other radio frequency component.

In some embodiments, the term "transitioning object" refers to an intake object that is transitioned from a first physical position to one or more second physical positions within a distribution system. A transitioning object, for example, may refer to a distribution object at and/or between one or more second phases of a distribution process. In some examples, a transitioning object may include one of a plurality of transitioning objects that are grouped into a subset of an object set. By way of example, an object set of a plurality of intake objects may be divided into one or more subsets that may be independently moved across a distribu- tion system. Each of the one or more subsets of the object set may include a respective plurality transitioning objects that may be jointly moved from a first physical position to one or more second physical positions within a distribution system.

In some embodiments, a number of a plurality of transi- tioning objects within a subset of the object set is based on one or more second physical positions to which the plurality of transitioning objects is moved. For example, as described herein, an intermediate destination for the plurality of tran- sitioning objects may include distribution canister that is associated with a fill threshold. In some examples, a plural- ity of transitioning objects may include a number of transi- tioning objects that comply with the fill threshold. In some examples, the plurality of intake objects is separated into a plurality of subsets of transitioning objects to tailor a num- ber of objects independently transported within a distribu- tion system to a fill threshold of a corresponding distribution canister.

In some examples, each of the subsets of transitioning objects is positioned (e.g., dispensed, etc.) within a respec- tive transitioning container that may be physically moved, tracked, and/or the like across one or more positions within a distribution system.

In some embodiments, the term "transitioning data object" refers to a data entity corresponding to a plurality of transitioning objects. A transitioning data object, for example, may include a data structure representing one or more aspects of a subset of a plurality of intake objects, such as a subset of tablets portioned out from a tablet lot as described herein with respect to a healthcare distribution system.

In some embodiments, a transitioning data object includes a plurality of transitioning attributes associated with a plu- rality of transitioning objects. For instance, a plurality of transitioning attributes may initially include a transition identifier and/or an intake identifier corresponding to the plurality of transitioning objects. For example, the transition and intake identifiers may be assigned to a transitioning data object to link (e.g., through a first data marriage operation) (i) a transitioning data object representing a plurality of transitioning objects that are a subset of a plurality of intake objects to (ii) an intake data object representing the plurality of intake objects. In some examples, a transition identifier may be assigned to an intake data object to mutually link the two data objects. In this manner, a transitioning data object and/or intake data object may incorporate attributes from each other to jointly track a subset of transitioning objects as they are moved across a distribution system.

As described herein, a transitioning data object may be modified throughout a distribution process to track the plurality of transitioning objects as they traverse a distribu- tion system. By way of example, a transitioning data object may be augmented with one or more location and/or con- tainer-based identifiers that respectively identify a physical location at and/or within which at least one transitioning object of the plurality of transitioning objects is positioned, disposed, placed, and/or the like. In this manner, using some of the techniques of the present disclosure, small, untrace- able, distribution objects, such as medications, and/or the like, may be tracked through chains of identifiers stored within the transitioning data object, the intake data object, and/or the like.

In some examples, a plurality of transitioning attributes may include one or more contextual attributes associated with the plurality of transitioning objects. The contextual attributes, for example, may include an object count that identifies number of a plurality of transitioning objects, and/or the like. In some examples, the object count may be generated during one or more dispensing operations in which a plurality of transitioning objects is separated from the plurality of intake objects and placed in a respective transitioning container. In some examples, a transitioning data object may be generated in response to, subsequent to, and/or prior to the one or more dispensing operations. By way of example, the transitioning data object may be gen- erated prior to the one or more dispensing operations and then updated with an object count subsequent to the one or more dispensing operations.

In some embodiments, the term "dispensing operation" refers to a computing-based task configured to initiate dispensation of one or more intake objects. For example, a dispensing operation may include initiating, controlling, and/or causing an object counting device, such as a tablet counting device, etc., to dispense a plurality of transitioning objects from a plurality of intake objects into a transitioning container. By way of example, in a healthcare distribution system, an object counting device may include an automatic and/or semi-automatic tablet counting machine. The object counting device, for example, may include a hopper (e.g., equipped with a vibration mechanism, etc.), a turntable, one or more object detection sensors (e.g., infrared sensors, weight sensors, image sensors, etc.), discharge funnels, and/or the like, that may be configured to collectively count and dispense a particular number of intake objects into a transitioning container. In some examples, an object count- ing device may output an object count for the plurality of transitioning objects.

In some embodiments, the term "transition identifier" refers to a data value (e.g., sequence of numeric, alpha- numeric characters, etc.) that identifies a transitioning data object. For example, the transition identifier may be an attribute of the transitioning data object that identifies the transitioning data object and/or the transitioning objects represented by the transitioning data object. A transition identifier, for example, may include a unique sequence of characters that are generated (e.g., randomly, in accordance with one or more constraints, etc.) to identify a transitioning data object.

In some embodiments, the term "transitioning container" refers to a physical container within which a plurality of transitioning objects is placed. For example, a transitioning container may include a cup, bottle, vial, package, intermediate bulk container, drum, insulated and/or refrigerated container, and/or the like. In some examples, a transitioning container may include a sealed package that may contain a plurality of transitioning objects in a tamper-proof environment. A sealed package may include any physical material configured to hold a plurality of objects, such as a sealed cup (e.g., metal, plastic, etc.), and/or the like. By way of example, a plurality of transitioning objects may be dispensed into an open transitioning container that, once filled, may be sealed using a container seal.

In some embodiments, a transitioning container includes a transitioning container label that is attached, disposed, affixed, and/or the like to an exterior surface of the transitioning container. In some examples, one or more transitioning attributes of a transitioning data object may be identified based on scanned indicia data generated by scanning at least a portion of a transitioning container label with a scanning device.

In some embodiments, the term "transitioning container label" refers to an identifier representation for a transition container. An identifier representation, for example, may include a scannable indicium that is attached, disposed, affixed, and/or the like to an exterior surface of the transitioning container.

In some embodiments, the term "container seal" refers to a physical barrier configured to enclose a transitioning container. For instance, a container seal may include a film (e.g., a plastic film, etc.) disposed over an opening of a transitioning container to enclose an interior compartment of the transitioning container. In this manner, a container seal may form a physical barrier between a plurality of transitioning objects within a transitioning container and an exterior environment.

A container seal may include any material and may be applied using any seal application processes. By way of example, a container seal may include a plastic film that is adhered over an opening of a transitioning container using a cup sealing machine, such as an automatic and/or manual plastic cup sealing machine and/or the like that may be configured to adhere a plastic film over a transitioning container (e.g., a plastic cup, etc.) by heating and melting at least one of the plastic film or transitioning container and placing each component together to form a hermetic seal.

In some embodiments, the term "backstop location" refers to a physical location of a distribution system. For instance, a backstop location may include a static, bulk storage portion of a distribution system. In some examples, a backstop location may be one of a plurality of backstop locations that specifies a granular location within a backstop storage area of a distribution system. By way of example, backstop storage area may include a three-dimensional storage area (e.g., embodied by a plurality adjacent shelving units, etc.) with one or more vertical, horizontal, and/or depth axes. A backstop location may identify relative coordinates of a physical location within a backstop storage area. The relative coordinates may describe a vertical coordinate (e.g., a level of rows, etc.), a horizontal coordinate (e.g., a position on a particular row), and/or a depth coordinate (e.g., a shelving unit), and/or the like.

In some embodiments, a backstop location may include a backstop identifier representation for backstop location. A backstop identifier representation, for example, may include a scannable indicium that is attached, disposed, affixed, and/or the like to an exterior surface of the backstop location.

In some embodiments, the term "backstop data object" refers to a data entity corresponding to a backstop location. A backstop data object, for example, may include a data structure representing one or more aspects of a backstop location, such as one or more relative coordinates, an availability status, object characteristics, and/or the like.

In some embodiments, a backstop data object includes a plurality of backstop attributes. For instance, a plurality of backstop attributes may include a backstop identifier, a transition identifier, and/or an intake identifier corresponding to a transitioning container stored at a backstop location. For example, the transition and intake identifiers may be assigned to a backstop data object to at least temporarily link (e.g., through a second data marriage operation) (i) a backstop data object to (ii) a transitioning data object representing a plurality of transitioning objects that are a subset of a plurality of intake objects and/or (iii) an intake data object representing the plurality of intake objects. For example, a transition identifier and/or intake identifier may be assigned to a backstop data object to temporarily link a plurality of transitioning objects to a physical backstop location. For instance, the transition and/or intake identifiers may be assigned in response to a placement of a transitioning container at a backstop location. In this manner, a location of a transitioning container may be recorded that enables the location tracking of a plurality of transitioning objects within the transitioning container.

In some embodiments, a backstop data object is modified throughout a distribution process to track the plurality of transitioning objects as they traverse a distribution system. By way of example, in response to physical removal of a transitioning container from the backstop location, a backstop data object may be modified (e.g., through a first data divorce operation) to remove transition and/or intake identifiers from the backstop data object. In this manner, using some of the techniques of the present disclosure, small, untraceable, distribution objects, such as medications, and/or the like, may be tracked through chains of identifiers temporarily stored within a backstop data object and/or the like. In some examples, in response to removing the transition and/or intake identifiers from the backstop data object, a historic tuple may be generated and stored in a compliance dataset to record a previous location of a transitioning container and/or a plurality of transitioning objects stored therein.

In some embodiments, the term "backstop identifier" refers to a data value (e.g., sequence of numeric, alphanumeric characters, etc.) that identifies a backstop data object. For example, the backstop identifier may be an attribute of the backstop data object that identifies the backstop data object and/or the relative coordinates represented by the backstop data object. A backstop identifier, for example, may include a unique sequence of characters that are assigned (e.g., randomly, in accordance with one or more constraints, etc.) to identify a backstop data object.

In some embodiments, the term "historic tuple" refers to two or more identifiers. For example, the historic tuple may include a plurality of currently and/or previously linked identifiers. In some examples, each historic tuple may identify a previous location of a distribution object within a distribution system.

In some embodiments, the term "compliance dataset" refers to a dataset for a distribution system. For example, a compliance dataset may include a plurality of historic tuples respectively corresponding to a plurality of a different distribution objects and/or groupings thereof. The plurality of historic tuples may define a sequence of locations for a respective distribution object as the object is moved across a distribution system.

In some embodiments, the term "predicted fill request" refers to a data entity that defines a future request to perform a fill operation for a robotic distribution device. A predicted fill request may be initiated in response to simulation data for a robotic distribution device. The simulation data, for example, may simulate a plurality of orders throughout a future time period to forecast an allocation of a target object. A predicted fill request may be initiated in response to a forecasted distribution of a target object exceeding an availability of a target object at a robotic distribution device. A predicted fill request may include a target object identifier that identifies a target object and/or one or more contextual attributes. The contextual attributes, for example, may identify a predicted fill time for the robotic distribution device and/or the like.

In some embodiments, one or more distribution operations are performed in response to a predicted fill request. For example, in response to a predicted fill request, a transitioning container may be identified for the target object and transitioned to an intermediate location of the distribution system to more efficiently access the target object when needed by the robotic distribution device. In some examples, an intermediate location may include a conveyor pallet of a conveyance assembly.

In some embodiments, the term "target object identifier" refers to a data value (e.g., sequence of numeric, alphanumeric characters, etc.) that identifies a distribution object and/or type of distribution object that is requested by a distribution operation, such as a fill operation, an order packaging operation, and/or the like. A target object identifier, for example, may include an object identifier, an intake identifier, and/or any other identifier described herein.

In some embodiments, the term "conveyance assembly" refers to a mechanical conveyance assembly configured to automatically and/or semi-automatically transport a plurality of transitioning containers from a plurality of backstop locations to one or more robotic distribution devices. A conveyance assembly, for example, may include a plurality of conveyor rollers (e.g., straight, tapered, concave, etc.), conveyor belts, actuation devices (e.g., motors, pulley systems, belt supports, drive units, etc.), and/or the like that collectively move a plurality of conveyor pallets from a first position to a second position, for example, that is closer to a robotic distribution device. In some examples, a conveyance assembly may be communicatively connected (e.g., through one or more wired and/or wireless communication interfaces, etc.) to one or more control interfaces. In some examples, the control interfaces may receive one or more movement instructions configured to control a movement of one or more conveyor pallets of the conveyance assembly.

In some embodiments, the term "conveyor pallet" refers to a mechanical support that is movably positioned, disposed, and/or affixed to a conveyance assembly. A conveyor pallet may include a dynamic, intermediate storage portion of a distribution system. In some examples, a conveyor pallet may be one of a plurality of conveyor pallets that specifies a movable location within a conveyance assembly of a distribution system. By way of example, the conveyor pallet may include one or more latches, tracks, and/or any other mechanism for movably coupling the conveyor pallet to a portion of a conveyance assembly.

In some embodiments, a conveyor pallet includes a plurality of transitioning container supports each configured to hold, grip, support, and/or receive a transitioning container. In some examples, a conveyor pallet may include a pallet identifier representation. A pallet identifier representation, for example, may include a scannable indicium that is attached, disposed, affixed, and/or the like to an exterior surface of the conveyor pallet. In some examples, a pallet identifier representation may be attached, disposed, affixed, and/or the like to an exterior side of a floor portion of the conveyor pallet. For instance, the pallet identifier representation may be faced downward with respect to the conveyor pallet towards a conveyance assembly such that sensors of a conveyance assembly may read the pallet identifier representation.

In some embodiments, the term "pallet data object" refers to a data entity corresponding to a conveyor pallet. A pallet data object, for example, may include a data structure representing one or more aspects of a conveyor pallet, such as one or more transition identifier, conveyor location identifiers, and/or the like. For instance, a pallet data object may define a two-dimensional intermediate storage location with one or more vertical and horizontal axes to define a relative position of a plurality of transitioning containers disposed on a respective conveyor pallet. In some examples, a pallet data object may include one or more transition identifiers that are assigned to one or more relative coordinates of the two-dimensional intermediate storage location.

In some embodiments, a pallet data object includes a plurality of pallet attributes. For instance, a plurality of pallet attributes may include a pallet identifier and/or one or more transition identifiers or intake identifiers corresponding to one or more transitioning containers disposed on a respective conveyor pallet. For example, the transition and intake identifiers may be assigned to a pallet data object to at least temporarily link (e.g., through a data marriage operation) (i) a pallet data object to (ii) a transitioning data object representing a plurality of transitioning objects that are a subset of a plurality of intake objects and/or (iii) an intake data object representing the plurality of intake objects. For example, a transition identifier and/or intake identifier may be assigned to a pallet data object to temporarily link a plurality of transitioning objects to a moveable location on a conveyance assembly. For instance, the transition and/or intake identifiers may be assigned in response to a placement of a transitioning container at a position on a conveyor pallet. In this manner, a location of a transitioning container may be recorded that enables the location tracking of a plurality of transitioning objects within the transitioning container.

In some embodiments, a pallet data object is modified throughout a distribution process to track the plurality of transitioning objects as they traverse a distribution system. By way of example, in response to physical removal of a transitioning container from the conveyor pallet, a pallet data object may be modified (e.g., through a second data divorce operation) to remove transition and/or intake identifiers from the pallet data object. In this manner, using some of the techniques of the present disclosure, small, untraceable, distribution objects, such as medications, and/or the like, may be tracked through chains of identifiers temporarily stored within a pallet data object and/or the like. In some examples, in response to removing the transition and/or intake identifiers from the pallet data object, a historic tuple may be generated and stored in a compliance dataset to record a previous location of a transitioning container and/or a plurality of transitioning objects stored therein.

In some embodiments, the term "pallet identifier" refers to a data value (e.g., sequence of numeric, alpha-numeric characters, etc.) that identifies a pallet data object. For example, the pallet identifier may be an attribute of the pallet data object that identifies the pallet data object and/or the relative coordinates represented by the pallet data object. A pallet identifier, for example, may include a unique sequence of characters that are assigned (e.g., randomly, in accordance with one or more constraints, etc.) to identify a pallet data object.

In some embodiments, the term "pallet identifier representation" refers to an identifier representation for conveyor pallet. An identifier representation, for example, may include a scannable indicium that is attached, disposed, affixed, and/or the like to an exterior surface of the conveyor pallet.

In some embodiments, the term "conveyor location identifier" refers to data value (e.g., sequence of numeric, alpha-numeric characters, etc.) that identifies a relative location of a conveyance assembly. By way of example, a conveyance assembly may include a plurality of scanning devices disposed at one or more different positions along the conveyance assembly. In some examples, each conveyor location identifier may correspond a particular position of the conveyance assembly at which a scanning device is disposed.

In some embodiments, a pallet identifier representation of a conveyor pallet is scanned in the event that the conveyor pallet is positioned over a scanning device located at a particular position. In response to scanning a pallet identifier representation, a pallet data object may be identified and modified to include (e.g., add a new identifier, replace an existing identifier, etc.) a conveyor location identifier corresponding to the particular position. In this manner, a conveyor pallet and/or one or more different transitioning container and/or transitioning data objects thereof may be tracked as the conveyor pallet is moved across a distribution system.

In some embodiments, the term "conveyor dataset" refers to a dataset for a conveyance assembly that represents a plurality of conveyer pallets and/or relative locations thereof with respect to the conveyance assembly. For example, a conveyor dataset may include a plurality of pallet data objects respectively corresponding to a plurality of conveyor pallets of the conveyance assembly.

In some embodiments, the term "real time fill request" refers to a data entity that defines a request to perform a fill operation for a robotic distribution device. A fill request may be initiated in response to a predicted allocation of a target object exceeding an availability of the target object at a robotic distribution device. A fill request may include a target object identifier that identifies a target object and/or one or more contextual attributes. The contextual attributes, for example, may identify a fill time for the robotic distribution device, a distribution canister of the robotic distribution device, and/or the like.

In some embodiments, one or more distribution operations are performed in response to a real time fill request. For example, in response to a real time fill request, a transitioning container may be identified for the target object and transitioned to an identified robotic distribution device. In some examples, a plurality of transitioning objects may be transitioned from the transitioning container to a distribution canister of the robotic distribution device.

In some embodiments, the term "fill operation" refers to a computing-based task configured to increase a number of target objects within a distribution canister of a robotic distribution device. For example, a fill operation may include initiating, controlling, and/or causing a robotic distribution device, such as a tablet counting device, etc., to eject a distribution canister corresponding to a target object. In addition, or alternatively, a fill operation may include initiating a movement of a transitioning container from an intermediate location, such as a conveyor pallet to a robotic distribution device. In some examples, a fill operation may include filling a distribution canister with a plurality of transitioning objects within a transitioning container.

In some embodiments, the term "robotic distribution device" refers to a computing device with one or more hardware and/or software components collectively configured to allocate distribution objects from a plurality of distribution canisters to single use packages, such as pouch containers. A robotic distribution device, for example, may include one or more pouch packaging machines, such as Veluwse Machine Industrie's INDIVION® machine. The robotic distribution device may include one or more mechanical arms that may be configured to interact with a plurality of object-specific distribution canisters to automatically dispense distribution objects into single use packaging. By way of example, in a healthcare distribution system, a robotic distribution device may handle a plurality of tablet-specific distribution canisters to create single dose, multi dose, and/or the like pouches.

In some embodiments, the term "manual retrieval notification" refers to a user interface notification that represents one or more portions of a fill operation. For example, manual retrieval notification may include a visual representation, provided through one or more user interfaces, of a transitioning container, a distribution canister, and/or any other information associated with a fill operation. By way of example, a manual retrieval notification may include a transition identifier, a canister identifier, and/or a pallet location representation that represents a current location of a transitioning container corresponding to the transition identifier.

In some embodiments, the term "pallet location representation" refers to a visual representation of a conveyor pallet. A pallet location representation may include a conveyance assembly overlay that may be overlaid to a conveyance assembly background. A pallet location representation may include an interactive icon that represents a relative location of a conveyor pallet relative to a conveyance assembly. A pallet location representation, for example, may be based on a conveyor location identifier corresponding to a pallet data object.

In some embodiments, the term "distribution canister" refers to a physical container corresponding to a robotic distribution device. A distribution canister may include a plurality of transitioned objects that may be distributed into single- and multi-dose packages. For example, a distribution canister may include an object-specific canister that is compatible with a robotic distribution device and a target object. In some examples, a distribution canister may include a physical barrier configured to at least partially enclose an interior chamber. In some examples, the physical barrier may include an aperture that is tailored to a specific target object to ensure a distribution of a single object at a time. By way of example, in a healthcare distribution system, a distribution canister may be tailored to a particular tablet capsule such that a single tablet exits the distribution canister at a particular point in time.

In some embodiments, a distribution canister includes a canister label that is attached, disposed, affixed, and/or the like to an exterior surface of the distribution canister. In some examples, one or more canister attributes of a canister data object may be identified based on scanned indicia data generated by scanning at least a portion of a canister label with a scanning device.

In some embodiments, the term "canister data object" refers to a data entity corresponding to a distribution canister. A canister data object, for example, may include a data structure representing one or more aspects of a distribution canister, such as a canister identifier, a corresponding object identifier, a fill level, and/or the like.

In some embodiments, a canister data object includes a plurality of canister attributes. For instance, a plurality of canister attributes may include a canister identifier and/or one or more transition identifiers or intake identifiers corresponding to one or more transitioning containers, and/or the like. For example, the transition and/or intake identifiers may be assigned to a canister data object to at least temporarily link (e.g., through a data marriage operation) (i) a canister data object to (ii) a transitioning data object representing a plurality of transitioning objects that are a subset of a plurality of intake objects and/or (iii) an intake data object representing the plurality of intake objects. For example, a transition identifier and/or intake identifier may be assigned to a canister data object to temporarily link a plurality of transitioning objects to a distribution location within a robotic distribution device. For instance, the transition and/or intake identifiers may be assigned in response to filling a distribution canister with at least a portion of a transitioning container. In this manner, a distribution canister may be at least temporarily linked to a transitioning data object. As described herein, by doing so one or more compliance operations may be performed to verify a correct movement of a plurality of transitioned objects from a first (e.g., backstop location) to second position (e.g., distribution canister).

In some embodiments, the term "canister identifier" refers to a data value (e.g., sequence of numeric, alpha-numeric characters, etc.) that identifies a canister data object. For example, the canister identifier may be an attribute of the canister data object that identifies the canister data object. A canister identifier, for example, may include a unique sequence of characters that are generated (e.g., randomly, in accordance with one or more constraints, etc.) to identify a canister data object.

In some embodiments, the term "compliance operation" refers to a computing-based task configured to investigate a compliance of a plurality of transitioning objects that are moved from a first to second location of a distribution system. A compliance operation, for example, may be configured to detect a discrepancy between a plurality of transitioning objects at a first location relative to the plurality of transitioning objects at the second location. For instance, in a regulatory environment such as a healthcare distribution system, regulated objects may be subjected to strict compliance guidelines in which missing objects may be investigated to prevent abuse and/or fraudulent behavior. To enable such investigations, a compliance operation may be configured to compare a first object count (e.g., from a transitioning data object) associated with a first location (e.g., a backstop location) with a second object count determined at a second location (e.g., a robotic distribution device). In some examples, a second object count may be determined using one or more weighing operations. A compliance operation may include a verified operation and/or an error operation in response to a comparison between a first and second object count.

In some embodiments, the term "weighing operation" refers to a computing-based task configured to generate weight data for a container of a distribution system and/or one or more contents of a container. A weighing operation, for example, may include applying one or more weighting scales, sensors, and/or the like to a container, such a distribution canister, to generate weight data for the container and/or one or more contents therein.

In some embodiments, the term "weight data" refers to a data value that represents a physical weight of physical entity, such as a distribution canister filled with a plurality of transitioning objects. Weight data may include any unit of measurement including one or more metric units (e.g., grams, etc.), imperial units (e.g., ounces, pounds, etc.), and/or the like.

In some examples, weight data may correspond to a plurality of transitioning objects within a distribution canister. Weight data, for example, may include a gross weight (e.g., excluding a weight of the distribution canister) of the plurality of transitioning objects within a distribution canister. In some examples, a second object count may be determined based on a comparison between the gross weight and an average weight of a respective distribution object within the distribution canister (e.g., as identified from a manufacturing attributes of a respective intake data object).

In some embodiments, the term "error operation" refers to a type of compliance operation that is initiated in response to a discrepancy between a first object count and a second object count. In response to a discrepancy, one or more error operations may be initiated to track one or more historical locations of the plurality of transitioning objects (e.g., via the compliance dataset, etc.). In some examples, an error operation may initiate a manual count of the plurality of transition objects, a deviation alert, and/or prevent a use of the distribution canister.

In some embodiments, the term "deviation alert" refers to a user interface notification that represents a discrepancy between a first and second object count. For example, deviation alert may include a visual representation, provided through one or more user interfaces, of a distribution canister, one or more previous locations of the plurality of transitioned object within the distribution canister, and/or any other information associated with an error operation. By way of example, a deviation alert may include a transition identifier, a canister identifier, a backstop identifier, an intake identifier, a pallet identifier, and/or any other identifier described herein.

In some embodiments, the term "verified operation" refers to a type of a compliance operation that is initiated in response to a verification that a first object count matches a second object count. In response to a verification that a first object count matches a second object count, one or more verified operations may include initiating one or more distribution tasks for allocating one or more of the transitioned objects from the distribution canister to one or more pouch containers, as described herein. In addition, or alternatively, a verified operation may include an initiation of one or more verification alerts, and/or the like.

In some embodiments, the term "ordered data object" refers to a data entity corresponding to a delivery request for one or more single-use packages of one or more target objects. An ordered data object, for example, may include a data structure representing one or more target objects (e.g., including one or more object identifiers, etc.), one or more individual usage authorizations (e.g., a dosage, a number of daily intakes, etc.) for the one or more target objects, one or more member attributes (e.g., a delivery address, member name, etc.), and/or the like. In some examples, an ordered data object may include an order identifier including a unique sequence of characters that identify a respective deliver request.

In some embodiments, the term "ordered object" refers to a packaged distribution object for exiting a distribution system. An ordered object, for example, may refer to a distribution object at the final phase, such as a portion of a pick, pack, and ship phase, of a distribution process. In some examples, an ordered object may include one of a plurality of ordered objects that are grouped into a single use object set for at-home delivery and consumption. A single use object set, for example, may include one or more ordered objects grouped into a single use package, such as a pouch container.

In some embodiments, the term "pouch container" refers to a physical container to which at least a portion of a plurality transitioned objects may be dispensed to create a single use package. For example, a pouch container may include a plastic pouch, bag, receptacle, and/or the like. In some examples, a pouch container may include a sealed package that includes one or more distribution objects corresponding to a single use of the distribution objects for a member. For example, in healthcare distribution system, a pouch container may include a plastic pouch including one or more tablet capsules prescribed for a single at home intake by a member of a healthcare system. In some examples, a plurality of pouch containers may be packaged together to generate multi-dose packages for a member over a time period.

In some embodiments, the term "pouch data object" refers to a data entity corresponding to one or more ordered objects and a corresponding order data object. A pouch data object, for example, may include a data structure representing one or more aspects of one or more ordered objects and/or an order for the ordered objects.

In some embodiments, a pouch data object includes a plurality of pouch attributes associated with the ordered objects. For instance, a plurality of pouch attributes may include a pouch identifier, intake identifier, a transition identifier, an order identifier, and/or the like. In this manner, attributes accumulated for ordered objects (e.g., with respect to an intake, transitioning, and/or counterparts) may be linked to a single use package for the ordered objects.

In some embodiments, the term "pouch identifier" refers to a data value (e.g., sequence of numeric, alpha-numeric characters, etc.) that identifies a pouch data object. For example, the pouch identifier may be an attribute of the pouch data object that identifies the pouch data object and/or the ordered objects represented by the pouch data object. A pouch identifier, for example, may include a unique sequence of characters that are generated (e.g., randomly, in accordance with one or more constraints, etc.) to identify a pouch data object.

IV. OVERVIEW

Embodiments of the present disclosure present object monitoring, visualization, and control techniques within an end-to-end automated distribution environment that enable the comprehensive and intelligent tracking of small objects. For example, some techniques of the present disclosure enable the facilitation of end-to-end dispensing operations for a fully automated multi-dose fulfillment process through container tracking user interfaces and series of virtually linked containers. The connected containers are leveraged to individually track and move small objects to and through an end-to-end conveyance assembly. For example, small sets of objects may be tracked as the objects are transitioned between multiple containers by "marrying" the objects (and/or virtual representations thereof) to different containers and then tracking the real time, historical, and predicted locations of the containers. This, in turn, enables real time tracking of small objects that are incapable of being individually tracked through traditional means, such a RFID tags, and/or other mediums that cannot be directly applied to small surface areas. Ultimately, the techniques of the present disclosure improve processing efficiencies, automation processes, and object throughput with respect to traditional distribution systems, while enabling the safe, secure, and compliant distribution of small objects subject to security measures.

Examples of technologically advantageous embodiments of the present disclosure include: (i) data object mapping techniques for automated object aggregation, storage, and tracking, (ii) automated object transitioning and optimal object selection techniques, (iii) automated cross-facility, cross-container object validation, among others. Other technical improvements and advantages may be realized by one of ordinary skill in the art.

V. EXAMPLE SYSTEM OPERATIONS

As indicated, various embodiments of the present disclosure make important technical contributions to object tracking, monitoring, and verification in an end-to-end distribution process. In particular, systems and methods are disclosed herein that leverage unique identifier mappings to link various containers, object sets, and/or attributes thereof across a multi-stage process. Unlike traditional techniques, some of the techniques of the present disclosure enable the reliable, safe, and efficient allocation of small object subject to security measures.

Figure 3:
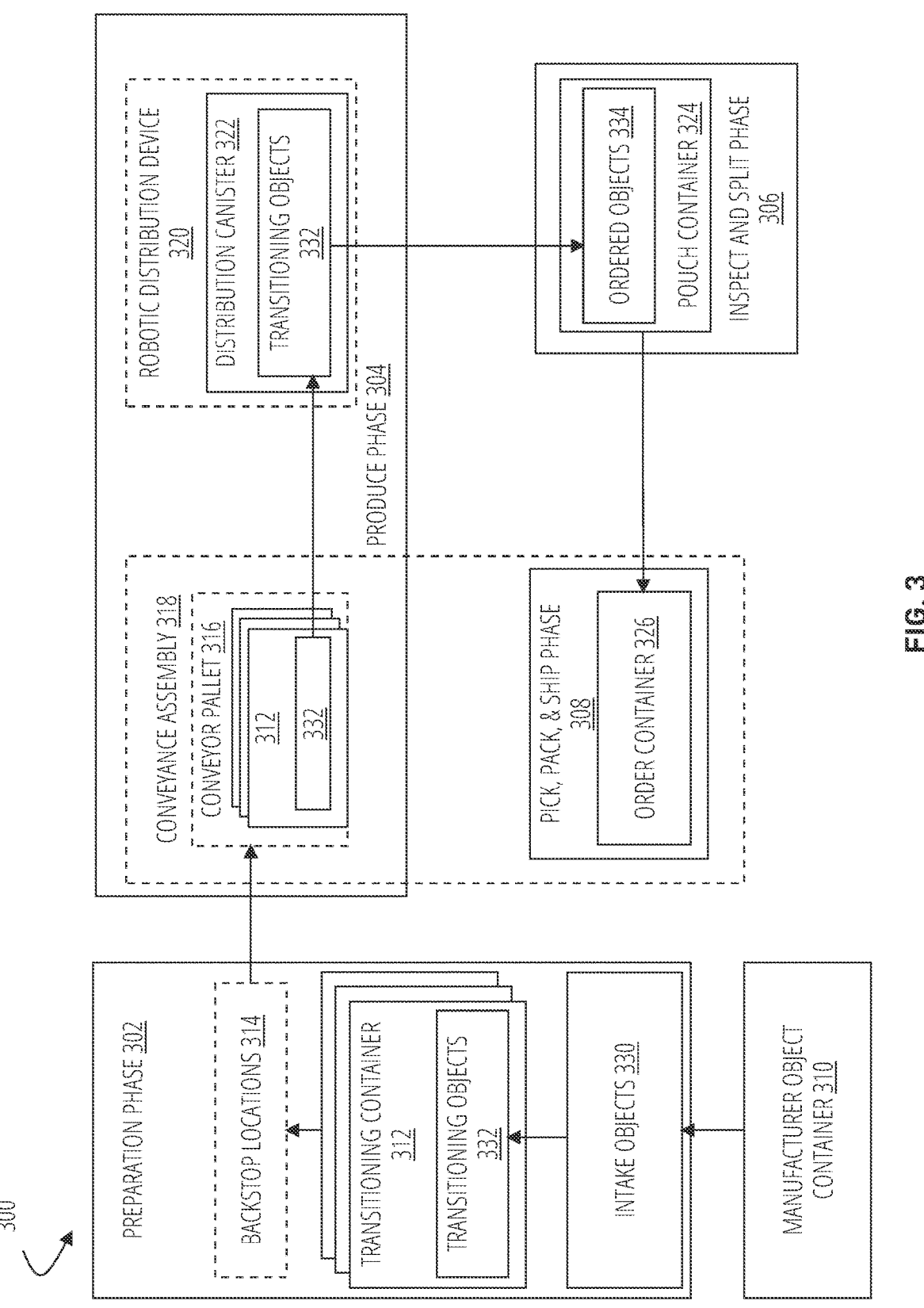
FIG. 3 is a process diagram showing an example multiphase distribution process for allocating distribution objects in accordance with some embodiments discussed herein.

FIG. 3 is a process diagram showing an example multi-phase distribution process 300 for allocating distribution objects in accordance with some embodiments discussed herein. As depicted, the multi-phase distribution process 300 includes a plurality of phases during which a plurality of distribution objects is transitioned between a plurality of different containers, locations, and devices. In traditional distribution processes with large objects, tracking individual objects is possible through individual object level tracking. However, such techniques are not practical for small objects, such as tablet capsules in a health care distribution system, among other small object examples. To address these technical challenges, the multi-phase distribution process 300 implements end-to-end custody tracking techniques for aggregating, tracking, and distributing portions of sets of small objects while maintaining comprehensive identifier chains linking ordered objects at a final phase of the multi-phase distribution process 300 (e.g., pick, pack, & ship phase 308, etc.) to an intake objects at an initial phase of the multi-phase distribution process 300 (e.g., preparation phase 302, etc.) and every phase therebetween (e.g., produce phase 304, inspect and split phase 306, etc.).

In some embodiments, the multi-phase distribution process 300 includes a preparation phase 302. During the preparation phase 302, one or more bulk-up operations may be performed to aggregate a plurality of distribution objects and prepare the distribution objects for transport across a distribution system. For example, the preparation phase 302 may include an initial phase during which a plurality of distribution objects is received from a manufacturer, aggregated into a plurality of intake objects 330, or an "object lot," divided into a set of pluralities of transitioning objects 332, each including a subset of the intake objects 330, that are then physically positioned at a respective backstop locations 314.

In some embodiments, an intake data object is generated by scanning manufacture information from a plurality of manufacturer object containers 310 and aggregating the scanned information into a single intake data object representing a plurality of intake objects.

In some embodiments, a distribution object is a physical entity that is processed by a distribution system. A distribution object may include any type of object that may be received, processed, and then dispatched by a distribution system to resolve an order. The type of distribution object may depend on the distribution system. As one example, for a healthcare distribution system, a distribution object may include a form of medication, such as a tablet, capsule, and/or the like, that may hold a particular dosage of elements prescribed for a member of a healthcare system. In such a case, the distribution object may be subject to strict regulations and security measures for ensuring that the correct object is provided to a correct member. At the same time, the distribution object may be limited in size, such that traditional forms of object tracking are unavailable to comply with the strict regulatory and security measures. Some of the techniques of the present disclosure may improve the distribution operations of traditional distribution systems to accommodate for unique characteristics, such as size and security constraints, of distribution objects, such as those used in healthcare systems.

In some embodiments, an intake object 330 is a distribution object at intake to a distribution system. An intake object 330, for example, may refer to a distribution object at the first phase, such as a portion of a preparation phase 302, of a multi-phase distribution process 300. In some examples, an intake object may include one of a plurality of intake objects 330 that are grouped into an object set to begin the multi-phase distribution process 300. The object set (e.g., an object lot), for example, may include a plurality of distribution objects aggregated from a plurality of different originating containers, such as the manufacturer object containers 310. The object set, for example, may be created at an initial phase of the multi-phase distribution process 300 to distribute objects that are traditionally distributed in bulk at a more granular, multi-dose level. By way of example, in a healthcare distribution system, an intake object may include an individual tablet from a tablet lot that includes a plurality of tablets aggregated from a plurality of manufacturer object containers 310 that allow the tablets to be uniformly transported and then redistributed into single, multi-dose packages, such as pouch containers 324, for at-home delivery and consumption.

In some embodiments, the manufacturer object container 310 is a physical container from which at least a portion of a plurality of intake objects 330 may be received. For example, a manufacturer object container 310 may include a bottle, vial, package, intermediate bulk container, drum, insulated and/or refrigerated container, and/or the like. In some examples, a manufacturer object container 310 may be received and/or processed (e.g., during a preparation phase 302) at a distribution system to generate a plurality of intake objects 330 for allocation across a plurality of orders. A manufacturer object container 310 may be received from an originating entity, such a manufacturer of the intake objects 330, an intermediary distribution entity, and/or the like.

In some embodiments, a plurality of transitioning data objects is generated from the intake data object. Each of the transitioning data objects, for example, may represent a plurality of transitioning objects 332. In some examples, each of the pluralities of transitioning objects 332 may be dispensed into a respective transitioning container 312 that may be moved to collectively move, track, and/or monitor a respective plurality of transitioning objects 332 as they traverse a distribution system.

In some embodiments, a transitioning object 332 is an intake object that is transitioned from a first physical position to one or more second physical positions within a distribution system. A transitioning object 332, for example, may refer to a distribution object at and/or between one or more second phases, such as the preparation phase 302 and produce phase 304, of the multi-phase distribution process 300. In some examples, a transitioning object may include one of a plurality of transitioning objects 332 that are grouped into a subset of an object set. By way of example, an object set of a plurality of intake objects 330 may be divided into one or more subsets that may be independently moved across a distribution system. Each of the one or more subsets of the object set may include a respective plurality transitioning objects 332 that may be jointly moved from a first physical position to one or more second physical positions within a distribution system.

In some embodiments, a number of a plurality of transitioning objects 332 within a subset of the object set is based on one or more second physical positions to which the plurality of transitioning objects 332 is moved. For example, as described herein, an intermediate destination for the plurality of transitioning objects 332 may include distribution canister 322 that is associated with a fill threshold. In some examples, a plurality of transitioning objects 332 may include a number of transitioning objects 332 that comply with the fill threshold. In some examples, the plurality of intake objects 330 is separated into a plurality of subsets of transitioning objects 332 to tailor a number of objects independently transported within a distribution system to a fill threshold of a corresponding distribution canister 322.

In some examples, each of the subsets of transitioning objects 332 is positioned (e.g., dispensed, etc.) within a respective transitioning container 312 that may be physically moved, tracked, and/or the like across one or more positions within a distribution system.

In some embodiments, a transitioning container 312 is a physical container within which a plurality of transitioning objects 332 is placed. For example, the transitioning container 312 may include a cup, bottle, package, vial, intermediate bulk container, drum, insulated and/or refrigerated container, and/or the like. In some examples, the transitioning container 312 may include a sealed package that may contain a plurality of transitioning objects 332 in a tamper-proof environment. A sealed package may include any physical material configured to hold a plurality of objects, such as a sealed cup (e.g., metal, plastic, etc.), and/or the like. By way of example, a plurality of transitioning objects 332 may be dispensed into an open transitioning container 312 that, once filled, may be sealed using a container seal.

In some embodiments, the container seal is a physical barrier configured to enclose the transitioning container 312 to create a tamper-proof environment. For instance, a container seal may include a film (e.g., a plastic film, etc.) disposed over an opening of the transitioning container 312 to at least partially enclose an interior compartment of the transitioning container 312. In this manner, a container seal may form a physical barrier between a plurality of transitioning objects 332 within the transitioning container 312 and an exterior environment.

A container seal may include any material and may be applied using any seal application processes. By way of example, a container seal may include a plastic film that is adhered over an opening of the transitioning container 312 using a cup sealing machine, such as an automatic and/or manual plastic cup sealing machine and/or the like that may be configured to adhere a plastic film over the transitioning container 312 (e.g., a plastic cup, etc.) by heating and melting at least one of the plastic film or transitioning container 312 and placing the components together to form a hermetic seal.

In some embodiments, a transitioning data object and/or intake data object is augmented with physical location data to record a storage location for a transitioning container 312. The storage location, for example, may include one of a plurality of backstop locations 314. For example, each transitioning container 312 may be stored at a physical backstop location 314. In some examples, the physical storage of a respective transitioning container 312 at a backstop location 314 may be represented through a data marriage which (i) a backstop identifier is assigned to a transitioning data object and/or intake data object and (ii) a transition identifier and/or intake identifier is assigned to a backstop data object. In some examples, the data marriage operation may be automatically initiated by scanning a backstop identifier representation and then scanning an individual transitioning container label.

In some embodiments, a backstop location is a physical location of a distribution system. For instance, a backstop location may include a static, bulk storage portion of a distribution system. In some examples, a backstop location may be one of a plurality of backstop locations 314 that specify a granular location within a backstop storage area of a distribution system. By way of example, backstop storage area may include a three-dimensional storage area (e.g., embodied by a plurality of adjacent shelving units, etc.) with one or more vertical, horizontal, and/or depth axes. The backstop locations 314 may identify relative coordinates of a physical location within the backstop storage area. The relative coordinates may describe a vertical coordinate (e.g., a row level, etc.), a horizontal coordinate (e.g., a position on a particular row), and/or a depth coordinate (e.g., a shelving unit), and/or the like.

In some embodiments, the multi-phase distribution process 300 includes a produce phase 304. During the produce phase 304, one or more prepare and/or transit operations may be performed to transition a plurality of distribution objects from the backstop locations 314 to a robotic distribution device 320 in an on-demand setting. To do so, one or more transitioning containers 312, each with a respective plurality of transitioning objects 332, may be placed on conveyor pallet 316 of a conveyance assembly 318. As described herein, in some examples, the transitioning container 312 may be moved from a backstop location 314 to a conveyor pallet 316 in response to a predicted fill request. In some examples, a data marriage operation may be performed, as described herein, to "marry" the transitioning data objects corresponding to the transitioning container 312 to pallet data objects corresponding to the conveyor pallet 316. At the same time, in some examples, the moved transitioning container 312 may be divorced from their respective backstop location 314 through a data divorce operation in which identifiers are removed from the backstop data objects corresponding to the respective backstop locations 314.

In some embodiments, a conveyance assembly 318 refers to a mechanical conveyor assembly configured to automatically and/or semi-automatically transport a plurality of transitioning containers 312 from a plurality of backstop locations 314 to one or more robotic distribution devices 320. The conveyance assembly 318, for example, may include a plurality of conveyor rollers (e.g., straight, tapered, concave, etc.), conveyor belts, actuation devices (e.g., motors, pulley systems, belt supports, drive units, etc.), and/or the like that collectively move a plurality of conveyor pallets 316 from a first position to a second position, for example, that is closer to a robotic distribution device 320. In some examples, the conveyance assembly 318 may be communicatively connected (e.g., through one or more wired and/or wireless communication interfaces, etc.) to one or more control interfaces. In some examples, the control interfaces may receive one or more movement instructions configured to control a movement of one or more conveyor pallets 316 of the conveyance assembly 318.

In some embodiments, the conveyor pallet 316 is a mechanical support that is movably positioned, disposed, and/or affixed to the conveyance assembly 318. The conveyor pallet 316, for example, may include a dynamic, intermediate storage portion of a distribution system. In some examples, the conveyor pallet 316 may be one of a plurality of conveyor pallets that specifies a movable location within the conveyance assembly 318 of a distribution system. By way of example, the conveyor pallet 316 may include one or more latches, tracks, and/or any other mechanism for movably coupling the conveyor pallet 316 to a portion of the conveyance assembly 318. In some embodiments, the conveyor pallet 316 includes a plurality of transitioning container supports each configured to hold, grip, support, and/or receive a transitioning container 312.

In some embodiments, an object location of the transitioning objects 332 placed on a conveyor pallet 316 are tracked using one or more pallet identifier representations of the conveyor pallet 316. The pallet identifier representations, for example, may be scanned as the conveyor pallet 316 is moved across the conveyance assembly 318 to identify a relative position of the conveyor pallet 316 relative to the conveyance assembly 318. In some examples, one or more instructions may be sent to the conveyance assembly 318 to instruct one or more actuators of the conveyance assembly 318 move the conveyor pallet 316 closer to a robotic distribution device 320 over time.

In some embodiments, a transitioning container 312 is identified from a conveyor pallet 316 for performing a fill operation for a distribution canister 322 of the robotic distribution device 320. For example, in response to a real time fill request, a transitioning container 312 may be intelligently identified, using some of the techniques of the present disclosure, for refilling a distribution canister 322 of the robotic distribution device 320 with the plurality of transitioning objects 332 within the transitioning container 312.

In some embodiments, the robotic distribution device 320 is a computing device with one or more hardware and/or software components collectively configured to allocate distribution objects from a plurality of distribution canisters 322 to single use packages, such as pouch containers 324. The robotic distribution device 320, for example, may include one or more pouch packaging machines, such as Veluwse Machine Industrie's INDIVION® machine. In some examples, the robotic distribution device 320 may include one or more mechanical arms that may be configured to interact with a plurality of object-specific distribution canisters to automatically dispense distribution objects into single use packaging. By way of example, in a health-care distribution system, the robotic distribution device 320 may handle a plurality of tablet-specific distribution canisters to create single dose, multi dose, and/or the like pouches.

In some embodiments, the distribution canister 322 is a physical container corresponding to a robotic distribution device 320. The distribution canister 322 may include a plurality of transitioned objects that may be distributed into single- and/or multi-dose packages. For example, a distribution canister 322 may include an object-specific canister that is compatible with a robotic distribution device 320 and a target object. In some examples, the distribution canister 322 may include a physical barrier configured to at least partially enclose an interior chamber. In some examples, the physical barrier may include an aperture that is tailored to a specific target object to ensure a distribution of a single object at a time. By way of example, in a healthcare distribution system, the distribution canister 322 may be tailored to a particular tablet capsule such that a single tablet exits the distribution canister 322 at a particular point in time.

In some embodiments, the multi-phase distribution process 300 includes an inspect and split phase 306. During the inspect and split phase 306, one or more operations may be performed to individually input one or more of the transitioning objects 332 into one or more multi-dose pouches to complete one or more order requests. For example, an order data object may be received and, in response to the order data object, the robotic distribution device 320 may be controlled to physically move a subset of ordered objects 334 from the transitioning objects 332 within the distribution canister 322 to one or more multi-dose pouches. The one or more multi-dose pouches, for example, may include a plurality of pouch containers configured to hold enough ordered objects for a single use.

In some embodiments, the ordered objects 334 include one or more packaged distribution objects that are packaged for exiting a distribution system. The ordered objects 334, for example, may refer to distribution objects at the final phase, such as a portion of the pick, pack, & ship phase 308, of the multi-phase distribution process 300. In some examples, the ordered objects 334 may include one or more of a plurality of ordered objects that are grouped into a single use object set for at-home delivery and consumption. A single use object set, for example, may include one or more ordered objects 334 grouped into a single use package, such as a pouch container 324.

In some embodiments, a pouch container 324 is a physical container to which at least a portion of a plurality transitioned objects may be dispensed to create a single use package. For example, the pouch container 324 may include a plastic pouch, bag, receptacle, and/or the like. In some examples, the pouch container 324 may include a sealed package that includes one or more distribution objects corresponding to a single use of the distribution objects for a member. For example, in healthcare distribution system, the pouch container 324 may include a plastic pouch including one or more tablet capsules prescribed for a single at home consumption by a member of a healthcare system. In some examples, a plurality of pouch containers 324 may be packaged together to generate multi-dose packages for a member over a time period.

In some embodiments, the multi-phase distribution process 300 includes a pick, pack, & ship phase 308. During the pick, pack, & ship phase 308, one or more pouch containers 324 may be linked (e.g., through one or more data marriage operations, etc.) to an order container 326 (e.g., a distribution tote, etc.), for example, by scanning a pouch identifier representation and/or a tote identifier representation and assigning identifiers of the data objects corresponding to each container to a respective intake data object, transitioning data object, and/or each other.

In some embodiments, the order container 326 is placed on the conveyance assembly 318. Instructions may be provided to the conveyance assembly 318 to move to the order container 326 based on an order identifier corresponding to the order data object. At designated locations on the conveyance assembly 318, the tote identifier representation may be scanned to track the object location of the ordered objects 334 as they are moved within the order container 326.

In some embodiments, once the ordered objects 334 reach a packaging station of the distribution system, the tote is emptied and the ordered objects 334 are packaged and shipped to a member corresponding to the order request. During this phase, tote identifier representation may be scanned to identify corresponding data objects (e.g., intake data objects, transitioning data objects, etc.) and a literature pack may be printed for the pouch containers 324 that include information aggregated from the manufacturer (e.g., obtained from the manufacturer object container 310, etc.), the distribution system, and/or the order request.

In some embodiments, custody tracking techniques are implemented at each phase of the multi-phase distribution process 300 to track otherwise untraceable objects using virtual representations of the objects. By doing so, distribution objects may be automatically moved across a distribution system while achieving strict compliance standards. An example of a first phase will now further be described with reference to FIG. 4.

Figure 4:
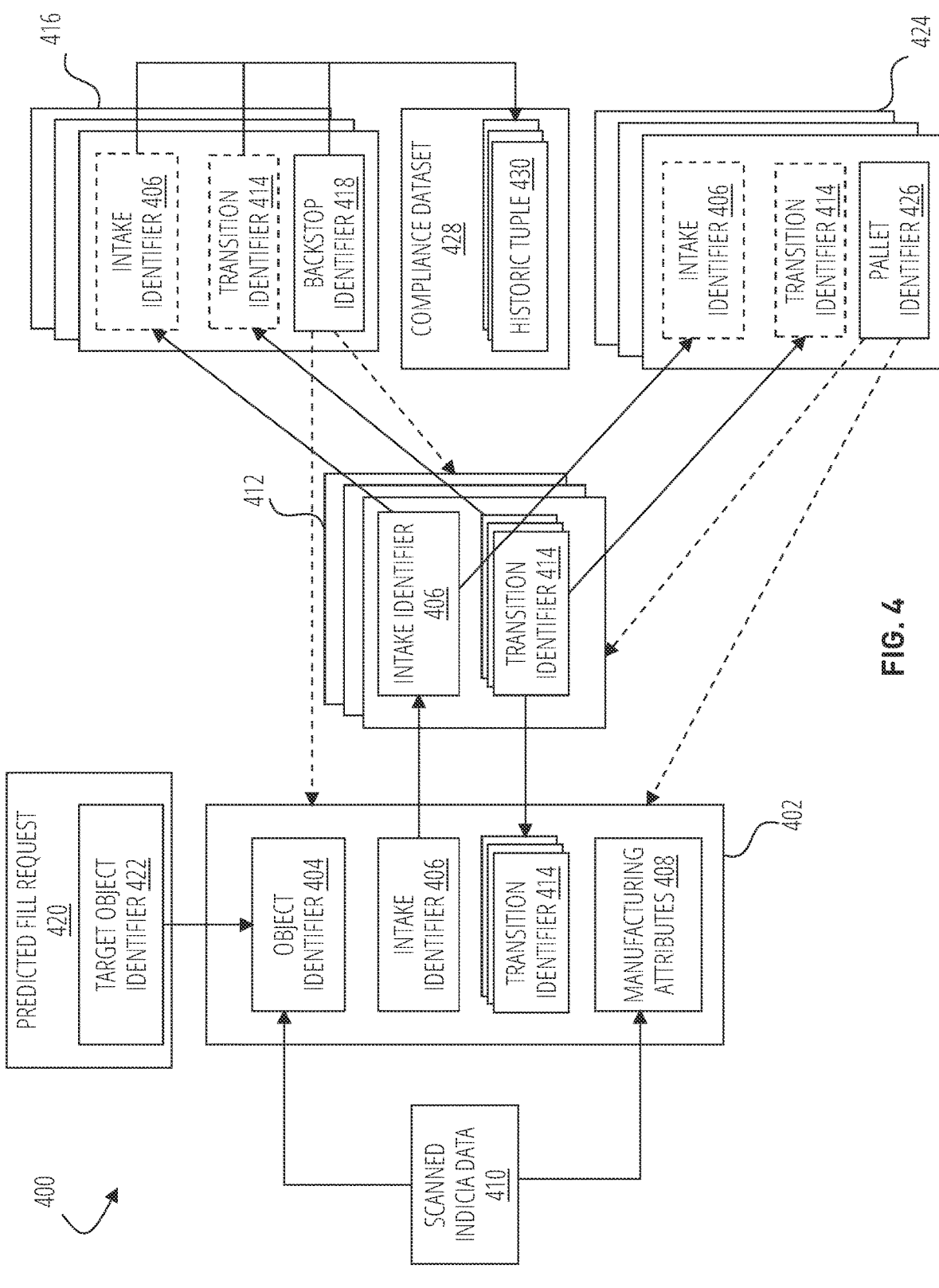
FIG. 4 is a dataflow diagram showing example data structures and modules for an automated object aggregation and storage technique in accordance with some embodiments discussed herein.

FIG. 4 is a dataflow diagram 400 showing example data structures and modules for an automated object aggregation and storage technique in accordance with some embodiments discussed herein. As depicted, an automated object aggregation and storage technique may leverage a plurality of data objects tailored to a distribution system to virtually assign identifiers across objects to both track and record object locations and other touchpoints. For example, using some of the techniques of the present disclosure, an intake data object 402 may be generated for a plurality of intake objects. The intake data object 402 may include an intake identifier 406 that may be passed, stored, and transferred across one or more data objects to track the movement of at least a portion of the plurality of intake objects as they are physically transported across a distribution system.

In some embodiments, an intake data object 402 is generated. The intake data object 402 may include an intake identifier 406 and an object identifier 404 respectively corresponding to a plurality of intake objects. In some examples, the object identifier 404 corresponds to an NDC.

In some embodiments, the object identifier 404 is a data value (e.g., sequence of numeric, alpha-numeric characters, etc.) that identifies a distribution object and/or type of distribution object. The object identifier 404, for example, may include a stock keeping unit (SKU), serial number, and/or the like for uniquely identifying a distribution object. The object identifier 404 may depend on the type of distribution object. For instance, in a healthcare system with regulated objects, the object identifier 404 may be a code, tag, and/or the like that is assigned by a regulatory body. By way of example, the object identifier 404 may include an NDC for a medication.

In some embodiments, the intake data object 402 is a data entity corresponding to a plurality of intake objects. The intake data object 402, for example, may include a data structure representing one or more aspects of a plurality of intake objects, such as a tablet lot aggregated from a plurality of different manufacturer object containers as described herein with respect to a healthcare distribution system.

In some embodiments, the intake data object 402 includes a plurality of intake attributes associated with a plurality of intake objects. For instance, a plurality of intake attributes may initially include an intake identifier 406 and/or an object identifier 404 corresponding to the plurality of intake objects. In addition, or alternatively, an intake data object 402 may include a plurality of manufacturing attributes 408 that describe one or more characteristics at least partially shared by the plurality of intake objects. Each of the manufacturing attributes 408, for example, may be derived from a respective manufacturing object container from which the plurality of intake objects is sourced.

As described herein, the intake data object 402 may be modified throughout a distribution process to track the plurality of intake objects and/or portions thereof as they traverse a distribution system. By way of example, the intake data object 402 may be augmented with one or more location and/or container-based identifiers that respectively identify a physical location at and/or within which at least one intake object of the plurality of intake objects is positioned, disposed, placed, and/or the like. In this manner, using some of the techniques of the present disclosure, small, untraceable, distribution objects, such as medications, and/or the like, may be tracked through chains of identifiers stored within the intake data object 402.

In some embodiments, the intake identifier 406 is a data value (e.g., sequence of numeric, alpha-numeric characters, etc.) that identifies the intake data object 402. For example, the intake identifier 406 may be an attribute of the intake data object 402 that identifies the intake data object 402 and/or the intake objects represented by the intake data object 402. The intake identifier 406, for example, may include a unique sequence of characters that are generated (e.g., randomly, in accordance with one or more constraints, etc.) to identify the intake data object 402 and/or link (e.g., marry, etc.) the intake data object 402 to one or more other data objects.

In some embodiments, the manufacturing attributes 408 are attribute associated with an intake object. For example, the manufacturing attributes 408 may define one or more characteristics of an intake object that are determined from a producer and/or originator of the intake object. By way of example, a manufacturing attributes 408 may be extracted from a manufacturer object container during an intake process of the intake object.

The manufacturing attributes 408 may include any type of object characteristic depending on the intake object and/or distribution system. As an example, for a healthcare distribution system, the manufacturing attributes 408 may include one or more medication attributes, such as a capsule weight (e.g., a weight of a single tablet, a set of tablets, etc.), expiration date, usage instructions, usage caution statements, physical drug description, dosage description, pharmaceutical manufacturer, and/or the like. In some examples, the manufacturing attributes 408 may be extracted from a manufacturer object container, such as a bulk drug container.

In some embodiments, the intake data object 402 is generated based on scanned indicia data 410. For example, the scanned indicia data 410 may be received, via one or more scanning operations. The scanned indicia data 410 may be associated with one or more manufacturer object containers. In some examples, the plurality of intake objects is received from one or more manufacturer object containers. In some examples, in response to the scanned indicia data 410, the intake data object 402 may be generated and assigned one or more manufacturing attributes 408 from the manufacturer object containers.

By way of example, a manufacturer object container may include an identifier representation. An identifier representation, for example, may include a scannable indicium that is attached, disposed, affixed, and/or the like to an exterior surface of the container, such as a manufacturer object container. In some examples, one or more manufacturing attributes 408 of an intake data object 402 may be identified based on scanned indicia data 410 generated by scanning the scannable indicium with a scanning device. In some examples, the intake data object 402 is generated in response to receiving scanned indicia data 410 from one or more manufacturing object containers.

In some embodiments, a scannable indicium is a physical representation of one or more computer readable media. A scannable indicium, for example, may include a quick response (QR) code, a bar code, and/or the like. In addition, or alternatively, a scannable indicium may include a radio frequency signal, such as one or more RFID signals emitted by one or more active and/or passive RFID tags (e.g., transponders, etc.), near field communication (NFC) signals emitted by one or more active and/or passive NFC tags, and/or the like.

In some embodiments, the scanned indicia data 410 is encoded and/or unencoded data that is generated responsive to one or more scanning operations for a scannable indicium. By way of example, scanned indicia data 410 may include an encoded and/or unencoded identifier that is reflective of a barcode, QR code, RFID, and/or the like. In addition, or alternatively, the scanned indicia data 410 may include one or more contextual attributes corresponding to the scanned indicium. The contextual attributes, for example, may be generated, received, and/or the like, using a lookup table and/or one or more other data structure based on an encoded and/or unencoded identifier extracted from a scannable indicium.

In some embodiments, a canning operation is a computing-based task configured to generate scanned indicia data 410. For example, the scanning operation may include the use of a scanning device to extract an encoded and/or unencoded identifier from a scannable indicium. In addition, or alternatively, a scanning operation may include one or more data collection operations for receiving contextual attributes corresponding to an encoded and/or unencoded identifier.

In some embodiments, a scanning device is a computing device with one or more hardware and/or software components collectively configured to generate scanned indicia data 410 from a scannable indicum. A scanning device, for example, may include an imaging scanner, a radio frequency reader, and/or the like. A scanning device may include one or more contact and/or non-contact scanners.

In some examples, a scanning device may include an imaging scanner that includes one or more image capturing devices (e.g., cameras, etc.), lighting devices (e.g., infrared lasers, etc.), and/or the like, collectively configured to generate an image of a scannable indicium and/or extract scanned indicia data from the image. By way of example, an imaging scanner may include barcode and/or QR code scanners, such as a laser scanner, pen wand, charge-coupled device (CCD) scanner, and/or the like.

In addition, or alternatively, a scanning device may include a radio frequency scanner that includes one or more radio frequency receivers, transponders, and/or the like that are collectively configured to detect a radio frequency signal from a scannable indicium and extract scanned indicia data 410 from the radio frequency signal. A radio frequency scanner, for example, may include a radio frequency readers configured to trigger, detect, and/or receive one or more radio frequency waves across one or more different wave lengths (e.g., low frequency bands, high frequency bands, etc.). By way of example, a radio frequency scanner may include one or more low frequency, high frequency, ultra-high frequency, and/or the like RFID readers, NFC readers, and/or any other radio frequency component.

In some embodiments, a transitioning data object 412 is generated using the intake data object 402. For example, a plurality of transitioning data objects 412 may be generated using the intake data object 402. Each transitioning data object 412 may correspond to a subset of the plurality of intake objects. In some examples, each transitioning data object 412 may include the intake identifier 406 and a respective transition identifier 414.

In some embodiments, the transitioning data object 412 is a data entity corresponding to a plurality of transitioning objects. A transitioning data object 412, for example, may include a data structure representing one or more aspects of a subset of a plurality of intake objects, such as a subset of tablets portioned out from a tablet lot as described herein with respect to a healthcare distribution system.

In some embodiments, the transitioning data object 412 includes a plurality of transitioning attributes associated with a plurality of transitioning objects. For instance, a plurality of transitioning attributes may initially include a transition identifier 414 and/or an intake identifier 406 corresponding to the plurality of transitioning objects. For example, the transition identifier 414 and intake identifier 406 may be assigned to the transitioning data object 412 to link (e.g., through a first data marriage operation) (i) a transitioning data object 412 representing a plurality of transitioning objects that are a subset of a plurality of intake objects to (ii) the intake data object 402 representing the plurality of intake objects. In some examples, a transition identifier 414 may be assigned to the intake data object 402 to mutually link (e.g., marry) the two data objects. In this manner, the transitioning data object 412 and/or intake data object 402 may incorporate attributes from each other to jointly track a subset of transitioning objects as they are moved across a distribution system.

As described herein, the transitioning data object 412 may be modified throughout a distribution process to track the plurality of transitioning objects as they traverse a distribution system. By way of example, the transitioning data object 412 may be augmented with one or more location and/or container-based identifiers that respectively identify a physical location at and/or within which at least one transitioning object of the plurality of transitioning objects is positioned, disposed, placed, and/or the like. In this manner, using some of the techniques of the present disclosure, small, untraceable, distribution objects, such as medications, and/or the like, may be tracked through chains of identifiers stored within the transitioning data object 412, the intake data object 402, and/or the like.

In some examples, a plurality of transitioning attributes may include one or more contextual attributes associated with the plurality of transitioning objects. The contextual attributes, for example, may include an object count that identifies number of a plurality of transitioning objects, and/or the like. In some examples, the object count may be generated during one or more dispensing operations in which a plurality of transitioning objects is separated from the plurality of intake objects and placed in a respective transitioning container. In some examples, the transitioning data object 412 may be generated in response to, subsequent to, and/or prior to the one or more dispensing operations. By way of example, the transitioning data object 412 may be generated prior to the one or more dispensing operations and then updated with an object count subsequent to the one or more dispensing operations.

In some embodiments, a dispensing operation is a computing-based task configured to initiate dispensation of one or more intake objects. For example, a dispensing operation may include initiating, controlling, and/or causing an object counting device, such as a tablet counting device, etc., to dispense a plurality of transitioning objects from a plurality of intake objects into a transitioning container. By way of example, in a healthcare distribution system, an object counting device may include an automatic and/or semi-automatic tablet counting machine. The object counting device, for example, may include a hopper (e.g., equipped with a vibration mechanism, etc.), a turntable, one or more object detection sensors (e.g., infrared sensors, weight sensors, image sensors, etc.), discharge funnels, and/or the like, that may be configured to collectively count and/or dispense a particular number of intake objects into a transitioning container. In some examples, an object counting device may output an object count for the plurality of transitioning objects.

In some embodiments, the transition identifier 414 is a data value (e.g., sequence of numeric, alpha-numeric characters, etc.) that identifies the transitioning data object 412. For example, the transition identifier 414 may be an attribute of the transitioning data object 412 that identifies the transitioning data object 412 and/or the transitioning objects represented by the transitioning data object 412. The transition identifier 414, for example, may include a unique sequence of characters that are generated (e.g., randomly, in accordance with one or more constraints, etc.) to identify the transitioning data object 412.

In some embodiments, in response to generating the transitioning data object 412, a plurality of subsets of the plurality of intake objects are dispensed into respective transitioning containers. For example, for each transitioning data object 412, a transitioning container label may be generated for a respective transitioning container based on the transitioning data object 412. The transitioning container label may include scanning indicia representing the transition identifier 414. In some examples, a dispensation of a respective subset of the plurality of intake objects may be initiated to the transitioning container. In some examples, an application of the transitioning container label may be initiated to the transitioning data object. In some examples, an application of a container seal may further be initiated to the transitioning container.

In some embodiments, a transitioning container includes a transitioning container label that is attached, disposed, affixed, and/or the like to an exterior surface of the transitioning container. In some examples, one or more transitioning attributes of a transitioning data object 412 may be identified based on scanned indicia data generated by scanning at least a portion of a transitioning container label with a scanning device. For example, the transitioning container label may be an identifier representation for the transition container. The identifier representation, for example, may include a scannable indicium that is attached, disposed, affixed, and/or the like to an exterior surface of the transitioning container.

In some embodiments, the intake data object 402 is modified with the transition identifier 414. For example, the intake data object 402 may be modified with each transition identifier 414 of the plurality of transition identifiers 414.

In some embodiments, a backstop data object 416 that corresponds to a backstop location is modified with the transition identifier 414 and/or the intake identifier 406. For example, the backstop data object 416 may be modified prior to, subsequent to, or during an initiation of a movement of a transitioning container to the backstop location. For example, the backstop data object 416 may include a backstop identifier 418 that corresponds to the backstop location. In some examples, the transitioning data object 412 and/or the intake data object 402 may be modified with the backstop identifier 418.

In some embodiments, the backstop data object 416 is a data entity corresponding to a backstop location. A backstop data object 416, for example, may include a data structure representing one or more aspects of a backstop location, such as one or more relative coordinates, an availability status, object characteristics, and/or the like.

In some embodiments, the backstop data object 416 includes a plurality of backstop attributes. For instance, a plurality of backstop attributes may include a backstop identifier 418, a transition identifier 414, and/or an intake identifier 406 corresponding to a transitioning container stored at a backstop location. For example, the transition identifier 414 and the intake identifier 406 may be assigned to a backstop data object 416 to at least temporarily link (e.g., through a second data marriage operation) (i) a backstop data object 416 to (ii) a transitioning data object 412 representing a plurality of transitioning objects that are a subset of a plurality of intake objects and/or (iii) the intake data object 402 representing the plurality of intake objects. For example, the transition identifier 414 and/or intake identifier 406 may be assigned to a backstop data object 416 to temporarily link a plurality of transitioning objects to a physical backstop location. For instance, the transition identifier 414 and/or intake identifier 406 may be assigned in response to a placement of a transitioning container at a backstop location. In this manner, a location of a transitioning container may be recorded that enables the location tracking of a plurality of transitioning objects within the transitioning container.

In some embodiments, the backstop data object 416 is modified throughout a distribution process to track the plurality of transitioning objects as they traverse a distribution system. By way of example, in response to physical removal of a transitioning container from the backstop location, the backstop data object 416 may be modified (e.g., through a first data divorce operation) to remove transition identifier 414 and/or intake identifier 406 from the backstop data object 416. In this manner, using some of the techniques of the present disclosure, small, untraceable, distribution objects, such as medications, and/or the like, may be tracked through chains of identifiers temporarily stored within a backstop data object 416 and/or the like. In some examples, in response to removing the transition identifier 414 and/or intake identifier 406 from the backstop data object 416, a historic tuple 430 may be generated and stored in a compliance dataset 428 to record a previous location of a transitioning container and/or a plurality of transitioning objects stored therein.

In some embodiments, the backstop identifier 418 is a data value (e.g., sequence of numeric, alpha-numeric characters, etc.) that identifies the backstop data object 416. For example, the backstop identifier 418 may be an attribute of the backstop data object 416 that identifies the backstop data object 416 and/or the relative coordinates represented by the backstop data object 416. The backstop identifier 418, for example, may include a unique sequence of characters that are assigned (e.g., randomly, in accordance with one or more constraints, etc.) to identify the backstop data object 416.

In some embodiments, a backstop location may include a backstop identifier representation for backstop location. The backstop identifier representation, for example, may include a scannable indicium that is attached, disposed, affixed, and/or the like to an exterior surface of the backstop location.

In some embodiments, the intake data object 402, the transitioning data object 412, and/or the backstop data object 416 are modified in response to one or more scanning operations. For example, first scanned indicia data associated with the transitioning container may be received via one or more first scanning operations. In addition, or alternatively, second scanned indicia data associated with the backstop location may be received via one or more second scanning operations. In some examples, in response to the first scanned indicia data and the second scanned indicia data, the backstop data object 416 may be modified with the transition identifier 414 and the intake identifier 406.

In some embodiments, a predicted fill request 420 is received that identifies a target object identifier 422. In some examples, a movement of the transitioning container from the backstop location to a conveyor pallet may be initiated in response to the predicted fill request 420.

In some embodiments, the predicted fill request 420 is a data entity that defines a future request to perform a fill operation for a robotic distribution device. The predicted fill request 420 may be initiated in response to simulation data for a robotic distribution device. The simulation data, for example, may simulate a plurality of orders throughout a future time period to forecast an allocation of a target object. The predicted fill request 420 may be initiated in response to a forecasted distribution of a target object exceeding an availability of a target object at a robotic distribution device. The predicted fill request 420 may include a target object identifier 422 that identifies a target object and/or one or more contextual attributes. The contextual attributes, for example, may identify a predicted fill time for the robotic distribution device, and/or the like.

In some embodiments, one or more distribution operations are performed in response to the predicted fill request 420. For example, in response to the predicted fill request 420, a transitioning container may be identified for the target object and transitioned to an intermediate location of the distribution system to more efficiently access the target object when needed by the robotic distribution device. In some examples, an intermediate location may include a conveyor pallet of a conveyance assembly.

In some embodiments, the target object identifier 422 is a data value (e.g., sequence of numeric, alpha-numeric characters, etc.) that identifies a distribution object and/or type of distribution object that is requested by a distribution operation, such as a fill operation, an order packaging operation, and/or the like. The target object identifier 422, for example, may include an object identifier 404, an intake identifier 406, and/or any other identifier described herein.

In some embodiments, in response to the predicted fill request 420, a transitioning data object 412 may be identified from the plurality of transitioning data objects based on the target object identifier 422, the intake identifier 406, and/or the intake data object 402.

In some embodiments, in response to the predicted fill request 420, the intake identifier 406 and/or the transition identifier 414 are assigned (e.g., through a third data marriage operation, etc.) to a pallet data object 424 corresponding to a conveyor pallet. In addition, or alternatively, a pallet identifier 426 may be assigned to the intake data object 402 and/or transitioning data object 412.

In some embodiments, the pallet data object 424 is a data entity corresponding to a conveyor pallet. The pallet data object 424, for example, may include a data structure representing one or more aspects of a conveyor pallet, such as one or more transition identifiers 414, conveyor location identifiers, and/or the like. For instance, a pallet data object 424 may define a two-dimensional intermediate storage location with one or more vertical and horizontal axes to define a relative position of a plurality of transitioning containers disposed on a respective conveyor pallet. In some examples, the pallet data object 424 may include one or more transition identifiers 414 that are assigned to one or more relative coordinates of the two-dimensional intermediate storage location.

In some embodiments, the pallet data object 424 includes a plurality of pallet attributes. For instance, a plurality of pallet attributes may include the pallet identifier 426 and/or one or more transition identifiers 414 or intake identifiers 406 corresponding to one or more transitioning containers disposed on a respective conveyor pallet.

In some embodiments, the pallet identifier 426 is a data value (e.g., sequence of numeric, alpha-numeric characters, etc.) that identifies the pallet data object 424. For example, the pallet identifier 426 may be an attribute of the pallet data object 424 that identifies the pallet data object 424 and/or the relative coordinates represented by the pallet data object 424. A pallet identifier 426, for example, may include a unique sequence of characters that are assigned (e.g., randomly, in accordance with one or more constraints, etc.) to identify the pallet data object 424.

In some examples, the transition identifiers 414 and intake identifiers 406 may be assigned to a pallet data object 424 to at least temporarily link (e.g., through a fourth data marriage operation) (i) a pallet data object 424 to (ii) the transitioning data object 412 representing a plurality of transitioning objects that are a subset of a plurality of intake objects and/or (iii) the intake data object 402 representing the plurality of intake objects. For example, a transition identifier 414 and/or intake identifier 406 may be assigned to the pallet data object 424 to temporarily link a plurality of transitioning objects to a moveable location on a conveyance assembly. For instance, the transition identifier 414 and/or intake identifier 406 may be assigned in response to a placement of a transitioning container at a position on a conveyor pallet. In this manner, a location of a transitioning container may be recorded that enables the location tracking of a plurality of transitioning objects within the transitioning container.

In some embodiments, in response to the predicted fill request 420, the intake identifier 406 and the transition identifier 414 are removed from the backstop data object 416. In some embodiments, in response to removing the intake identifier 406 and the transition identifier 414 from the backstop data object 416, the transition identifier 414, the intake identifier 406, and/or the backstop identifier 418 are stored as a historic tuple 430.

In some embodiments, the historic tuple 430 include two or more identifiers. For example, the historic tuple 430 may include a plurality of currently and/or previously linked identifiers. In some examples, each historic tuple 430 may identify a previous location of a distribution object within a distribution system.

In some embodiments, the compliance dataset 428 is a dataset for a distribution system. For example, the compliance dataset 428 may include a plurality of historic tuples 430 respectively corresponding to a plurality of a different distribution objects and/or groupings thereof. The plurality of historic tuples 430 may define a sequence of locations for a respective distribution object as the object is moved across a distribution system.

In this manner, a location of a group of distribution objects, such as the transitioning objects described herein, may be tracked across a plurality of linked data structures, such as the compliance dataset 428, the intake data object 402, transitioning data object 412, backstop data object 416, pallet data object 424, and/or the like, to maintain accurate representations of both historical and real time locations of a group of objects too small to track using traditional techniques. By doing so, the distribution objects may be automatically and intelligently identified, on demand, from a backstop location and physically moved to a conveyance assembly while maintaining full control and visibility over the object's location. Once on the conveyance assembly, automated transitioning techniques may be applied, at one or more second phases, to transition the distribution objects from a transit state to a distribution state at which they may be individually segmented into single use packages. An example of such automated transitioning techniques will now further be described with reference to FIG. 5.

Figure 5:
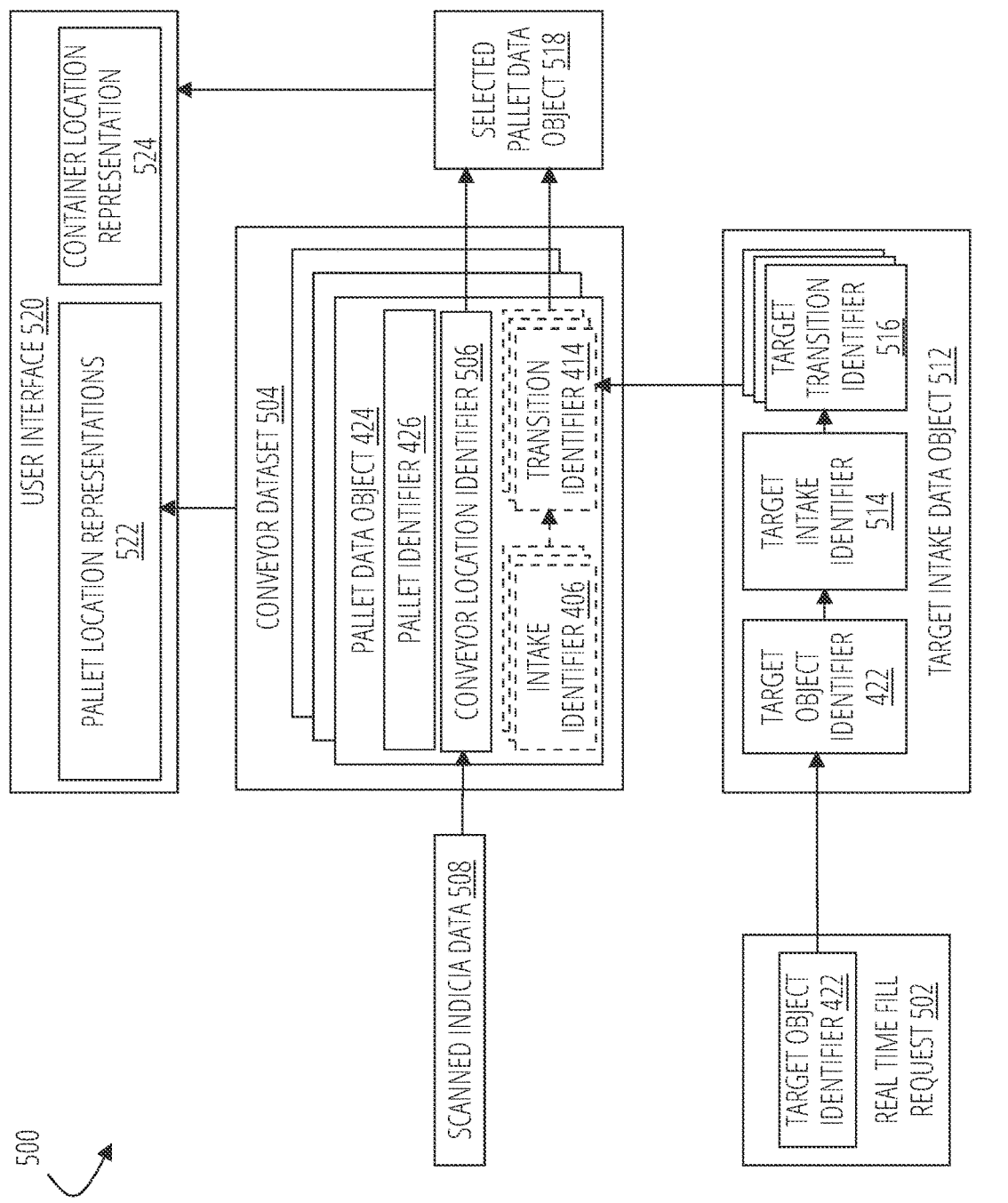
FIG. 5 is a dataflow diagram showing example data structures and modules for an automated object transitioning technique in accordance with some embodiments discussed herein.

FIG. 5 is a dataflow diagram 500 showing example data structures and modules for an automated object transitioning technique in accordance with some embodiments discussed herein. As depicted, an automated object transitioning technique may leverage a plurality of data objects tailored to a distribution system to virtually assign identifiers across objects to both track and record object locations and other touchpoints. Such data objects may be leveraged, in real time, to receive and resolve real time fill requests for a plurality of robotic distribution devices throughout an operational time period.

In some embodiments, a real time fill request 502 is received. The real time fill request 502 may be associated with a robotic distribution device. In some examples, the real time fill request 502 may include a target object identifier 422. In some examples, the real time fill request 502 may be based on a current object availability and/or a predicted object availability at the robotic distribution device.

In some embodiments, the real time fill request 502 is a data entity that defines a request to perform a fill operation for a robotic distribution device. The real time fill request 502 may be initiated in response to a predicted allocation of a target object exceeding an availability of the target object at a robotic distribution device. The real time fill request 502 may include a target object identifier 422 that identifies the target object and/or one or more contextual attributes. The contextual attributes, for example, may identify a fill time for the robotic distribution device, a distribution canister of the robotic distribution device, and/or the like.

In some embodiments, one or more distribution operations are performed in response to the real time fill request 502. For example, in response to the real time fill request 502, a transitioning container may be identified for the target object and transitioned to an identified robotic distribution device. In some examples, a plurality of transitioning objects may be transitioned from the transitioning container to a distribution canister of the robotic distribution device to complete a fill operation.

In some embodiments, the fill operation is a computing-based task configured to increase a number of target objects within a distribution canister of a robotic distribution device. For example, the fill operation may include initiating, controlling, and/or causing a robotic distribution device, such as a tablet counting device, etc., to eject a distribution canister corresponding to a target object. In addition, or alternatively, the fill operation may include initiating a movement of a transitioning container from an intermediate location, such as a conveyor pallet to a robotic distribution device. In some examples, the fill operation may include filling the distribution canister with a plurality of transitioning objects within a transitioning container.

In some embodiments, a conveyor dataset 504 may be accessed that corresponds to a conveyance assembly. The conveyor dataset 504 may include a plurality of pallet data objects 424. Each of the pallet data objects 424 may include one or more intake identifiers 406 and/or a conveyor location identifier 506. For example, each pallet data object 424 may include one or more transition identifiers 414 respectively corresponding to one or more transitioning containers physically disposed on the conveyor pallet.

In some embodiments, the conveyor dataset 504 is a dataset for the conveyance assembly that represents a plurality of conveyer pallets and/or relative locations thereof with respect to the conveyance assembly. For example, the conveyor dataset may include a plurality of pallet data objects 424 respectively corresponding to a plurality of conveyor pallets of the conveyance assembly.

In some embodiments, each of the one or more pallet data objects 424 include a respective conveyor location identifier 506. For example, the conveyor location identifier 506 may identify a relative location of a respective conveyor pallet relative to the conveyance assembly. In some examples, one or more pallet location representations 522 may be provided for display. For instance, via a user interface 520, one or more pallet location representations 522 may be provided that respectively correspond to each of the conveyor location identifiers 506 for each of the one or more pallet data objects 424.

In some embodiments, a conveyor location identifier 506 is a data value (e.g., sequence of numeric, alpha-numeric characters, etc.) that identifies a relative location of a conveyance assembly. By way of example, the conveyance assembly may include a plurality of scanning devices disposed at one or more different positions along the conveyor assembly. In some examples, each conveyor location identifier 506 may correspond a particular position of the conveyance assembly at which a scanning device is disposed.

For example, a conveyor pallet may include a pallet identifier representation. The pallet identifier representation may include an identifier representation for a conveyor pallet. An identifier representation, for example, may include a scannable indicium that is attached, disposed, affixed, and/or the like to an exterior surface of the conveyor pallet. The pallet identifier representation, for example, may include a scannable indicium that is attached, disposed, affixed, and/or the like to an exterior surface of the conveyor pallet. In some examples, the pallet identifier representation may be attached, disposed, affixed, and/or the like to an exterior side of a floor portion of the conveyor pallet. For instance, the pallet identifier representation may be faced downward with respect to the conveyor pallet towards a conveyance assembly such that sensors of a conveyance assembly may read the pallet identifier representation.

In some embodiments, a pallet identifier representation of a conveyor pallet is scanned in the event that the conveyor pallet is positioned over a scanning device located at a particular position. In response to scanning a pallet identifier representation, a pallet data object may be identified and modified to include (e.g., add a new identifier, replace an existing identifier, etc.) a conveyor location identifier corresponding to the particular position. In this manner, a conveyor pallet and/or one or more different transitioning container and/or transitioning data objects thereof may be tracked as the conveyor pallet is moved across a distribution system.

In some embodiments, the conveyor location identifier 506 corresponds to a previously scanned location within the conveyance assembly. For example, scanned indicia data 508 associated with a respective conveyor pallet may be received via one or more scanning operations performed at the previously scanned location. For instance, the scanned indicia data 508 may be scanned from a pallet identifier representation disposed on the respective conveyor pallet. In some examples, the conveyor location identifier 506 may be assigned to a pallet data object 424 of the respective conveyor pallet in response to the scanned indicia data 508.

In some embodiments, a pallet data object is selected from the plurality of pallet data objects 424 of the conveyor dataset 504 based on the target object identifier 422, the one or more intake identifiers 406, and/or the conveyor location identifier 506. For example, a target intake identifier 514 may be identified from the one or more intake identifiers 406 respectively corresponding to each of the plurality of pallet data objects 424 based on the target object identifier 422. By way of example, a target object identifier 422 may be leveraged to identify a target intake data object 512 that includes a corresponding target object identifier 422 and a target intake identifier 514 corresponding to the target object identifier 422. In some examples, one or more target transition identifiers 516 may be identified (e.g., using the target intake data object 512, etc.) based on the target intake identifier 514. The pallet data object 424 may be selected based on a comparison between the one or more transition identifiers 414 for each of the pallet data object 424 and the one or more target transition identifiers 516.

For example, the one or more transition identifiers 414 for a selected pallet data object 518 may include at least one of the one or more target transition identifiers 516. In some examples, one or more pallet data objects 424 from the conveyor dataset 504 may be identified that are each associated with a target transitioning identifier of the one or more target transition identifiers 516. In some examples, the selected pallet data object 518 may be selected from the pallet data objects 424 based on the conveyor location identifier 506. The selected pallet data object 518, for example, may be selected based on a relative distance between the selected pallet data object 518 and the robotic distribution device. In some examples, the selected pallet data object 518 may correspond to the conveyor pallet that is closest to the robotic distribution device.

In some embodiments, the performance of a fill operation may be initiated for the robotic distribution device based on the conveyor pallet of the conveyance assembly that corresponds to the selected pallet data object 518. In some examples, the fill operation may be initiated by providing, via the user interface 520, a manual retrieval notification including a pallet location representation corresponding to the conveyor location identifier of the selected pallet data object 518. In some examples, the manual retrieval notification may include a container location representation 524 corresponding to a container location identifier for a transitioning container positioned on the conveyor pallet. For example, the container location representation 524 may identify a relative location of a container location identifier relative to the selected conveyor pallet.

In some embodiments, the manual retrieval notification is a user interface notification that represents one or more portions of a fill operation. For example, manual retrieval notification may include a visual representation, provided through one or more user interfaces 520, of a transitioning container, a distribution canister, and/or any other information associated with a fill operation. By way of example, a manual retrieval notification may include a transition identifier 414, a canister identifier, and/or a pallet location representation 522 that represents a current location of a transitioning container corresponding to the transition identifier 414.

In some embodiments, the pallet location representation 522 to a visual representation of a conveyor pallet and/or location thereof. A pallet location representation 522 may include a conveyance assembly overlay that may be overlaid to a conveyance assembly background. A pallet location representation 522 may include an interactive icon that represents a relative location of a conveyor pallet relative to a conveyance assembly. The pallet location representation 522, for example, may be based on a conveyor location identifier 506 corresponding to a selected pallet data object 518.

In some embodiments, the fill operation is initiated by initiating a movement of the conveyor pallet corresponding to the selected pallet data object 518 based on a distance between the conveyor pallet and the robotic distribution device.

In some embodiments, the pallet data object 424 is modified throughout a distribution process to track the plurality of transitioning objects as they traverse a distribution system. By way of example, in response to physical removal of a transitioning container from the conveyor pallet, the pallet data object 424 may be modified (e.g., through a second data divorce operation) to remove transition identifiers 414 and/or intake identifiers 406 from the pallet data object 424. In this manner, using some of the techniques of the present disclosure, small, untraceable, distribution objects, such as medications, and/or the like, may be tracked through chains of identifiers temporarily stored within the pallet data object 424, and/or the like. In some examples, in response to removing the transition identifier 414 and/or intake identifier 406 from the pallet data object 424, a historic tuple 430 may be generated and stored in the compliance dataset 428 to record a previous location of the transitioning container and/or a plurality of transitioning objects stored therein.

In this manner, a group of distribution objects, such as the transitioning objects described herein, may be tracked across a plurality of linked data structures, such as the conveyor dataset 504, pallet data objects 424, intake data objects, and/or the like, to automatically and intelligently identify specific transitioning container, on demand, from a conveyance assembly incrementally transporting a plurality of visually similar transitioning containers. Once identified, automated object verification techniques may be applied, at one or more third phases, to ensure that the distribution objects transported from a first to second position within the distribution system adhere with one or more compliance standards. An example of such object verification techniques will now further be described with reference to FIG. 6.

FIG. 6 is a dataflow diagram 600 showing example data structures and modules for an automated object verification technique in accordance with some embodiments discussed herein. As depicted, an automated object verification technique may leverage a plurality of data objects tailored to a distribution system to virtually assign identifiers across objects to both track and record object locations and other touchpoints. Such data objects may be leveraged, in real time, to ensure compliance with one or more compliance standards, reduce object waste, identify fraudulent behavior, and improve transportation efficiencies for an automated distribution system.

In some embodiments, a transition identifier 414 is received that corresponds to a transitioning data object 412. As described herein, the transitioning data object 412 may include an intake identifier 406 corresponding to a plurality of transitioning data objects including the transitioning data object 412 and a pallet identifier 426 for a conveyor pallet configured to move the transitioning container across one or more portions of the distribution system. In some examples, scanned indicia data associated with the transitioning container may be received via one or more scanning operations. In some examples, the transition identifier 414 may be identified based on the scanned indicia data.

In some embodiments, the transitioning data object 412 includes a first object count 606. For example, the first object count 606 may identify a number of the plurality of transitioning objects (e.g., within a subset of a plurality of intake objects corresponding to the intake identifier 406, etc.) that are dispensed to a transitioning container. In some examples, the first object count 606 is determined during one or more dispensing operations of the subset of the plurality of intake objects.

In some embodiments, a canister identifier 604 is received that corresponds to a distribution canister. A canister identifier 604, for example, may be a data value (e.g., sequence of numeric, alpha-numeric characters, etc.) that identifies a canister data object 602. For example, the canister identifier 604 may be an attribute of the canister data object 602 that identifies the canister data object 602. The canister identifier 604, for example, may include a unique sequence of characters that are generated (e.g., randomly, in accordance with one or more constraints, etc.) to identify the canister data object 602.

In some embodiments, the canister data object 602 is a data entity corresponding to a distribution canister. The canister data object 602, for example, may include a data structure representing one or more aspects of the distribution canister, such as the canister identifier 604, a corresponding object identifier 404, a fill level, and/or the like.

In some embodiments, the canister data object 602 includes a plurality of canister attributes. For instance, a plurality of canister attributes may include the canister identifier 604 and/or one or more transition identifiers 414 or intake identifiers 406 corresponding to one or more transitioning containers, and/or the like. For example, the transition identifiers 414 and/or intake identifiers 406 may be assigned to the canister data object 602 to at least temporarily link (e.g., through a fifth data marriage operation) (i) a canister data object 602 to (ii) a transitioning data object 412 representing a plurality of transitioning objects that are a subset of a plurality of intake objects and/or (iii) an intake data object 402 representing the plurality of intake objects. For example, the transition identifier 414 and/or intake identifier 406 may be assigned to a canister data object 602 to temporarily link a plurality of transitioning objects to a distribution location within a robotic distribution device. For instance, the transition identifier 414 and/or intake identifier 406 may be assigned in response to filling a distribution canister with at least a portion of a transitioning container. In this manner, a distribution canister may be at least temporarily linked to a transitioning data object 412. As described herein, by doing so one or more compliance operations may be performed to verify a correct movement of a plurality of transitioned objects from a first (e.g., backstop location) to second position (e.g., distribution canister).

In some embodiment, scanned indicia data associated with the distribution canister is received via one or more scanning operations. For example, a distribution canister may include a canister label that is attached, disposed, affixed, and/or the like to an exterior surface of the distribution canister. In some examples, one or more canister attributes of a canister data object may be identified based on scanned indicia data generated by scanning at least a portion of a canister label with a scanning device. In some examples, the canister identifier 604 may be identified based on the scanned indicia data.

In some embodiments, in response to receiving the transition identifier 414 and the canister identifier 604 (e.g., within a time threshold, etc.), the transition identifier 414 and the intake identifier 406 of the transitioning data object 412 may be assigned (e.g., via the fifth data marriage operation, etc.) to the canister data object 602 corresponding to the distribution canister. In some examples, the transition identifier 414 and the canister identifier 604 may be received within a time threshold. The transition identifier 414 and/or the intake identifier 406, for example, may be assigned to the canister data object 602 based on the time interval.

In some embodiments, in response to receiving the transition identifier 414 and the canister identifier 604 (e.g., within a time threshold, etc.), the canister identifier 604 is assigned to an intake data object 402 corresponding to the intake identifier 406. In addition, or alternatively, the canister identifier 604 may be assigned to the transitioning data object 412.

In some embodiments, in response to receiving the transition identifier 414 and the canister identifier 604 (e.g., within a time threshold, etc.), the intake identifier 406 and the transition identifier 414 are removed from the pallet data object 424 corresponding to the pallet identifier 426. In some examples, the intake identifier 406, the transition identifier 414, and the pallet identifier 426 may be stored as a historic tuple 430 in a compliance dataset 428.

In some embodiments, a second object count 610 is determined that corresponds to the distribution canister. For example, weight data 608 may be received for the distribution canister via one or more weighing operations. In some examples, the second object count 610 may be based on the weight data 608 and the intake identifier 406. By way of example, the second object count 610 may be determined based on a comparison between a gross weight of the plurality of objects within the distribution canister and one or more manufacturing attributes 408 corresponding to the objects, such as an average object weight and/or the like.

In some embodiments, a weighing operation is a computing-based task configured to generate weight data 608 for a container of a distribution system and/or one or more contents of a container. The weighing operation, for example, may include applying one or more weighting scales, sensors, and/or the like to a container, such a distribution canister, to generate weight data 608 for the container and/or one or more contents therein.

In some embodiments, the weight data 608 is a data value that represents a physical weight of physical entity, such as a distribution canister filled with a plurality of transitioning objects. Weight data 608 may include any unit of measurement including one or more metric units (e.g., grams, etc.), imperial units (e.g., ounces, pounds, etc.), and/or the like.

In some examples, the weight data 608 may correspond to a plurality of transitioning objects within a distribution canister. Weight data 608, for example, may include a gross weight (e.g., excluding a weight of the distribution canister) of the plurality of transitioning objects within a distribution canister. In some examples, a second object count may be determined based on a comparison between the gross weight and an average weight of a respective distribution object within the distribution canister (e.g., as identified from manufacturing attributes 408 of a respective intake data object 402).

In some embodiments, a compliance operation 612 is initiated based on a comparison between the first object count 606 and the second object count 610. A compliance operation 612 may include one of (i) one or more verified operations initiated in response to the first object count 606 matching the second object count 610 and/or (ii) one or more error operations initiated in response to a deviation between the first object count 606 and the second object count 610.

In some embodiments, the compliance operation 612 is a computing-based task configured to investigate a compliance of a plurality of transitioning objects that are moved from a first to second location of a distribution system. The compliance operation 612, for example, may be configured to detect a discrepancy between a plurality of transitioning objects at a first location relative to the plurality of transitioning objects at the second location. For instance, in a regulatory environment such as a healthcare distribution system, regulated objects may be subjected to strict compliance guidelines in which missing objects may be investigated to prevent abuse and/or fraudulent behavior. To enable such investigations, the compliance operation 612 may be configured to compare a first object count (e.g., from a transitioning data object 412) associated with a first location (e.g., a backstop location) with a second object count 610 determined at a second location (e.g., a robotic distribution device). In some examples, a second object count 610 may be determined using one or more weighing operation. The compliance operation 612 may include a verified operation and/or an error operation in response to a comparison between the first object count 606 and/or the second object count 610.

In some embodiments, the one or more error operations include providing, via one or more user interfaces, a deviation alert indicative of the first object count 606, the second object count 610, the transitioning container, and/or the distribution canister.

In some embodiments, an error operation is a type of compliance operation 612 that is initiated in response to a discrepancy between the first object count 606 and the second object count 610. In response to a discrepancy, one or more error operations may be initiated to track one or more historical locations of the plurality of transitioning objects (e.g., via the compliance dataset 428, etc.). In some examples, the error operation may initiate a manual count of the plurality of transition objects, a deviation alert, and/or prevent a use of the distribution canister.

In some embodiments, a deviation alert is a user interface notification that represents a discrepancy between the first object count 606 and the second object count 610. For example, the deviation alert may include a visual representation, provided through one or more user interfaces, of a distribution canister, one or more previous locations of the plurality of transitioned object within the distribution canister, and/or any other information associated with an error operation. By way of example, a deviation alert may include a transition identifier 414, a canister identifier 604, a backstop identifier, an intake identifier 406, a pallet identifier 426, and/or any other identifier described herein.

In some embodiments, the one or more verified operations include handling an order request by allocating one or more of the plurality of transitioning objects from the distribution canister to one or more single use packages, such as one or more pouch containers. For example, in response to an order data object, a verified operation may include controlling, via a robotic distribution device, a dispensation of one or more ordered objects of the plurality of transitioning objects from a distribution canister to a pouch container. In some examples, the second object count 610 may be modified based on a third object count identifying a number of the one or more ordered objects dispensed. A pouch data object may be generated that includes the intake identifier 406, the third object count, and/or an order identifier corresponding to the order data object.

In some embodiments, the verified operation is a type of a compliance operation that is initiated in response to a verification that the first object count 606 matches the second object count 610. In response to a verification that the first object count 606 matches the second object count 610, one or more verified operations may include initiating one or more distribution tasks for allocating one or more of the transitioned objects from the distribution canister to one or more pouch containers, as described herein. In addition, or alternatively, the verified operation may include an initiation of one or more verification alerts, and/or the like.

In some embodiments, an ordered data object may be a data entity corresponding to a delivery request for one or more single-use packages of one or more target objects. An ordered data object, for example, may include a data structure representing one or more target objects (e.g., including one or more object identifiers, etc.), one or more individual usage authorizations (e.g., a dosage, a number of daily intakes, etc.) for the one or more target objects, one or more member attributes (e.g., a delivery address, member name, etc.), and/or the like. In some examples, an ordered data object may include an order identifier including a unique sequence of characters that identify a respective deliver request.

In some embodiments, a pouch data object is a data entity that corresponds to one or more ordered objects and a corresponding order data object. The pouch data object, for example, may include a data structure representing one or more aspects of one or more ordered objects and/or an order for the ordered objects.

In some embodiments, the pouch data object includes a plurality of pouch attributes associated with the ordered objects. For instance, a plurality of pouch attributes may include a pouch identifier, intake identifier 406, a transition identifier 414, an order identifier, and/or the like. In this manner, attributes accumulated for ordered objects (e.g., with respect to intake, transitioning, and/or other counterparts) may be linked to a single use package for the ordered objects.

In some embodiments, the pouch identifier is a data value (e.g., sequence of numeric, alpha-numeric characters, etc.) that identifies a pouch data object. For example, the pouch identifier may be an attribute of the pouch data object that identifies the pouch data object and/or the ordered objects represented by the pouch data object. A pouch identifier, for example, may include a unique sequence of characters that are generated (e.g., randomly, in accordance with one or more constraints, etc.) to identify a pouch data object.

Figure 7:
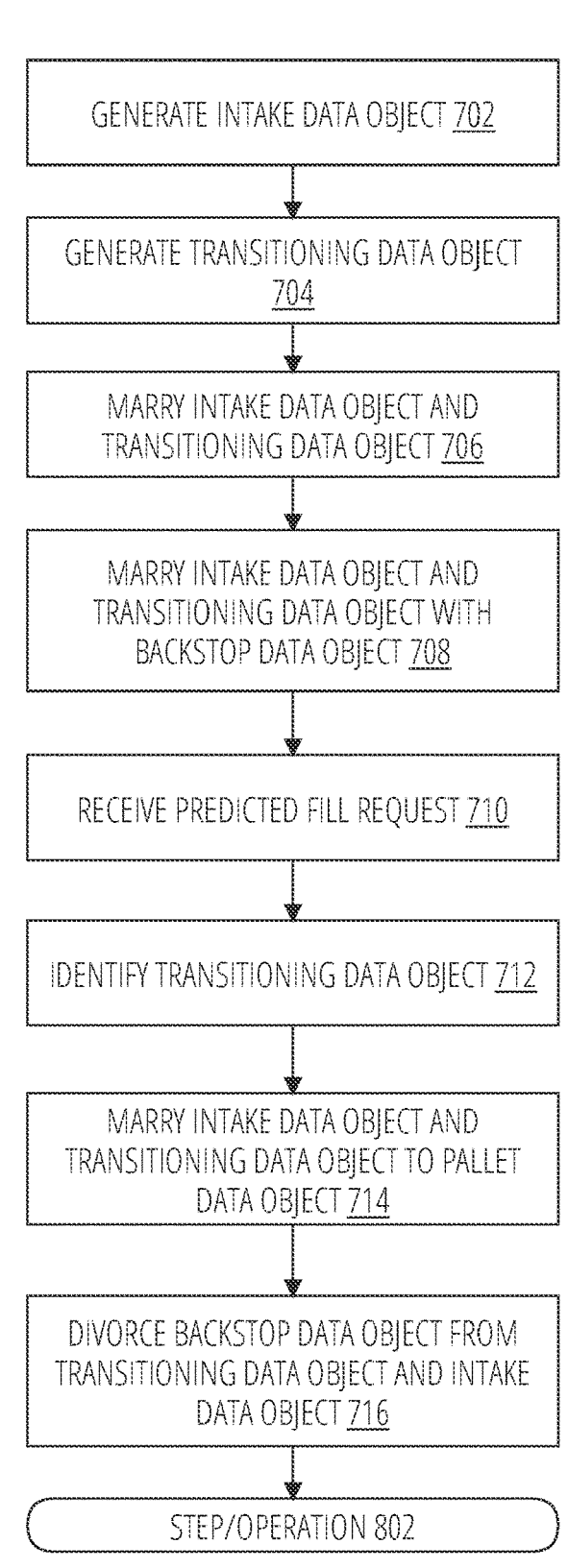
FIG. 7 is a flowchart showing an example of an automated object aggregation and storage process in accordance with some embodiments discussed herein.

FIG. 7 is a flowchart showing an example of an automated object aggregation and storage process in accordance with some embodiments discussed herein. The flowchart depicts a process 700 for improving the object monitoring, visualization, and control within an end-to-end automated distribution environment that enables the comprehensive and intelligent tracking of small objects that are resistant to traditional object tracking techniques. The process 700 may be implemented by one or more computing devices, entities, and/or systems described herein. For example, via the various steps/operations of the process 700, the computing system 100 may leverage improved object modeling, identifier mapping, and sensing techniques to dynamically track object locations through a series of containers and corresponding data objects. By doing so, the process 700 enables the real time and interactive tracking of small objects within a complex and automated distribution facility that empowers strict compliance with security measures for such objects, while improving processing efficiency, throughput, and maintenance of traditional distribution systems.

FIG. 7 illustrates an example process 700 for explanatory purposes. Although the example process 700 depicts a particular sequence of steps/operations, the sequence may be altered without departing from the scope of the present disclosure. For example, some of the steps/operations depicted may be performed in parallel or in a different sequence that does not materially impact the function of the process 700. In other examples, different components of an example device or system that implements the process 700 may perform functions at substantially the same time or in a specific sequence.

In some embodiments, the process 700 includes, at step/operation 702, generating an intake data object. For example, the computing system 100 may generate an intake data object including an intake identifier and/or an object identifier respectively corresponding to a plurality of intake objects. In some examples, the object identifier is an NDC.

In some examples, the computing system 100 may receive, via one or more scanning operations, scanned indicia data associated with one or more manufacturer object containers. In response to the scanned indicia data, the computing system 100 may generate the intake data object and assign one or more manufacturing attributes to the intake data object. In some examples, the plurality of intake objects is received from the one or more manufacturer object containers.

In some embodiments, the process 700 includes, at step/operation 704, generating a transitioning data object. For example, the computing system 100 may generate, using the intake data object, a transitioning data object corresponding to a subset of the plurality of intake objects and including the intake identifier and/or a transition identifier.

In some examples, in response to generating the transitioning data object, the computing system 100 may generate a transitioning container label for a transitioning container based on the transitioning data object. The transitioning container label may include scanning indicia representing the transition identifier. The computing system 100 may initiate a dispensation of the subset of the plurality of intake objects to the transitioning container. In some examples, the computing system 100 may initiate an application of the transitioning container label to the transitioning data object. In some examples, the computing system 100 may initiate an application of a container seal to the transitioning container.

In some embodiments, the process 700 includes, at step/operation 706, marrying the intake data object and/or the transitioning data object. For example, the computing system 100 may modify the intake data object with the transition identifier.

In some embodiments, the computing system 100 initiates a movement of the transitioning container to a backstop location.

In some embodiments, the process 700 includes, at step/operation 708, marrying the intake data object and/or the transitioning data object with a backstop data object. For example, the computing system 100 may modify the backstop data object with the transition identifier and/or the intake identifier. In some examples, the backstop data object includes a backstop identifier that corresponds to the backstop location. In some examples, the computing system 100 may modify the transitioning data object and/or the intake data object with the backstop identifier.

In some examples, the computing system 100 may receive, via one or more first scanning operations, first scanned indicia data associated with a transitioning container. The computing system 100 may receive, via one or more second scanning operations, second scanned indicia data associated with a backstop location. In some examples, in response to the first scanned indicia data and the second scanned indicia data, the computing system 100 may modify the backstop data object with the transition identifier and/or the intake identifier.

In some embodiments, the process 700 includes, at step/operation 710, receiving a predicted fill request. For example, the computing system 100 may receive a predicted fill request identifying a target object identifier. In some examples, the computing system 100 may initiate a movement of the transitioning container from the backstop location to a conveyor pallet in response to the predicted fill request.

In some embodiments, the process 700 includes, at step/operation 712, identifying a transitioning data object. For example, the computing system 100 may, in response to the predicted fill request, identify the transitioning data object based on the target object identifier, the intake identifier, and the intake data object.

In some embodiments, the process 700 includes, at step/operation 714, marrying the intake data object and/or the transitioning data object to a pallet data object. For example, the computing system 100 may, in response to the predicted fill request, assign the intake identifier and/or the transition identifier to a pallet data object corresponding to a conveyor pallet.

In some embodiments, the process 700 includes, at step/operation 716, divorcing the backstop data object from the intake data object and/or the transitioning data object. For example, the computing system 100 may, in response to the predicted fill request, remove the intake identifier and/or the transition identifier from the backstop data object.

In some examples, in response to removing the intake identifier and the transition identifier from the backstop data object, the computing system 100 may store the transition identifier, the intake identifier, and/or the backstop identifier as a historical tuple.

In some examples, the process 700 may continue as step/operation 802 of the process 800.

FIG. 8 is a flowchart showing an example of an automated object transitioning process 800 in accordance with some embodiments discussed herein. The flowchart depicts a process 800 for improving the object monitoring, visualization, and control within an end-to-end automated distribution environment that enables the comprehensive and intelligent tracking of small objects that are resistant to traditional object tracking techniques. The process 800 may be implemented by one or more computing devices, entities, and/or systems described herein. For example, via the various steps/operations of the process 800, the computing system 100 may leverage improved object modeling, identifier mapping, and sensing techniques to dynamically track object locations through a series of containers and corresponding data objects. By doing so, the process 800 enables the real time and interactive tracking of small objects within a complex and automated distribution facility that empowers strict compliance with security measures for such objects, while improving processing efficiency, throughput, and maintenance of traditional distribution systems.

FIG. 8 illustrates an example process 800 for explanatory purposes. Although the example process 800 depicts a particular sequence of steps/operations, the sequence may be altered without departing from the scope of the present disclosure. For example, some of the steps/operations depicted may be performed in parallel or in a different sequence that does not materially impact the function of the process 800. In other examples, different components of an example device or system that implements the process 800 may perform functions at substantially the same time or in a specific sequence.

In some embodiments, the process 800 may begin after step/operation 716 of the process 700 where the process 700 includes divorcing a backstop data object from a transitioning data object and/or an intake data object in response to a corresponding transitioning container being moved from a backstop location to a conveyor pallet.

In some embodiments, the process 800 includes, at step/operation 802, receiving a real time fill request. For example, the computing system 100 may receive a real time fill request associated with a robotic distribution device and including a target object identifier. The real time fill request, for example, may be based on a current object availability and/or a predicted object availability at the robotic distribution device.

In some embodiments, the process 800 includes, at step/operation 804, accessing a conveyor dataset. For example, the computing system 100 may access the conveyor dataset corresponding to a conveyance assembly and including a pallet data object including one or more intake identifiers and/or a conveyor location identifier. The conveyor location identifier, for example, identifies a relative location of the conveyor pallet relative to the conveyance assembly. For instance, the conveyor location identifier may correspond to a previously scanned location within the conveyance assembly. In some examples, the computing system 100 may receive, via one or more scanning operations performed at the previously scanned location, scanned indicia data associated with the conveyor pallet and, in response to the scanned indicia data, assign the conveyor location identifier to the pallet data object. In some examples, the scanned indicia data may be scanned from a pallet identifier representation disposed on the conveyor pallet.

In some examples, each of the one or more pallet data objects includes a respective conveyor location identifier. The computing system 100 may provide, via a user interface, one or more pallet location representations respectively corresponding to the respective conveyor location identifier for each of the one or more pallet data objects.

In some embodiments, the process 800 includes, at step/operation 806, selecting a pallet data object. For example, the computing system 100 may select the pallet data object from a plurality of other pallet data objects of the conveyor dataset based on the target object identifier, the one or more intake identifiers, and/or the conveyor location identifier. In some examples, each pallet data object includes one or more transition identifiers respectively corresponding to one or more transitioning containers physically disposed on a conveyor pallet. The computing system 100 may identify a target intake identifier based on the target object identifier, identify one or more target transition identifiers based on the target intake identifier, and then select the pallet data object based on a comparison between one or more transition identifiers and the one or more target transition identifiers.

By way of example, the one or more transition identifiers of the pallet data object may include at least one of the one or more target transition identifiers. The computing system 100 may identify one or more pallet data objects from the conveyor dataset that are each associated with a target transitioning identifier of the one or more target transition identifiers. In such a case, the computing system 100 may select the pallet data object from the one or more pallet data objects based on the conveyor location identifier.

In some embodiments, the process 800 includes, at step/operation 808, initiating a fill operation. For example, the computing system 100 may initiate the performance of the fill operation for the robotic distribution device based on the conveyor pallet of the conveyance assembly that corresponds to the pallet data object. For instance, the computing system 100 may provide, via a user interface, a manual retrieval notification including a pallet location representation corresponding to the conveyor location identifier. In some examples, the manual retrieval notification may include a container location representation corresponding to a container location identifier for a transitioning container positioned on the conveyor pallet and the container location representation may identify a relative location of the container location identifier relative to the conveyor pallet.

In addition, or alternatively, the computing system 100 may initiate a movement of the conveyor pallet based on a distance between the conveyor pallet and the robotic distribution device.

In some examples, the process 800 may continue as step/operation 902 of the process 900.

FIG. 9 is a flowchart showing an example of an automated object verification process 900 in accordance with some embodiments discussed herein. The flowchart depicts a process 900 for improving the object monitoring, visualization, and control within an end-to-end automated distribution environment that enables the comprehensive and intelligent tracking of small objects that are resistant to traditional object tracking techniques. The process 900 may be implemented by one or more computing devices, entities, and/or systems described herein. For example, via the various steps/operations of the process 900, the computing system 100 may leverage improved object modeling, identifier mapping, and sensing techniques to dynamically track object locations through a series of containers and corresponding data objects. By doing so, the process 900 enables the real time and interactive tracking of small objects within a complex and automated distribution facility that empowers strict compliance with security measures for such objects, while improving processing efficiency, throughput, and maintenance of traditional distribution systems.

FIG. 9 illustrates an example process 900 for explanatory purposes. Although the example process 900 depicts a particular sequence of steps/operations, the sequence may be altered without departing from the scope of the present disclosure. For example, some of the steps/operations depicted may be performed in parallel or in a different sequence that does not materially impact the function of the process 900. In other examples, different components of an example device or system that implements the process 900 may perform functions at substantially the same time or in a specific sequence.

In some embodiments, the process 900 may begin after step/operation 808 of the process 800 where the process 800 includes initiating a fill operation for a distribution canister of a robotic distribution device.

In some embodiments, the process 900 includes, at step/operation 902, receiving a transition identifier. For example, the computing system 100 may receive a transition identifier corresponding to a transitioning data object that includes (a) a first object count of a plurality of transitioning objects within a transitioning container, (b) an intake identifier corresponding to the plurality of transitioning objects, and/or (c) a pallet identifier for a conveyor pallet configured to move the transitioning container. For instance, the computing system 100 may receive, via one or more scanning operations, scanned indicia data associated with the transitioning container. In some examples, the computing system 100 may identify the transition identifier based on the scanned indicia data.

In some examples, the first object count may identify a number of the plurality of transitioning objects within a subset of a plurality of intake objects corresponding to the intake identifier. For example, the computing system 100 may determine the first object count during one or more dispensing operations of the subset of the plurality of intake objects.

In some embodiments, the process 900 includes, at step/operation 904, receiving a canister identifier. For example, the computing system 100 may receive a canister identifier corresponding to a distribution canister. For instance, the computing system 100 may receive, via one or more scanning operations, scanned indicia data associated with the distribution canister. In some examples, the computing system 100 may identify the canister identifier based on the scanned indicia data. In some examples, the transition identifier and the canister identifier are received within a time threshold.

In some embodiments, the process 900 includes, at step/operation 906, marrying a canister data object to an intake data object and/or a transitioning data object. For example, the computing system 100 may, in response to receiving the transition identifier and/or the canister identifier, assign the transition identifier and/or the intake identifier to a canister data object corresponding to the distribution canister and assign the canister identifier to a target intake data object corresponding to the intake identifier.

In some embodiments, the process 900 includes, at step/operation 908, divorcing a pallet data object from the intake data object and/or the transitioning data object. For example, the computing system 100 may, in response to receiving the transition identifier and/or the canister identifier, remove the intake identifier and/or the transition identifier from a pallet data object corresponding to the pallet identifier. In some examples, the computing system 100 may store the intake identifier, the transition identifier, and/or the pallet identifier as a historic tuple.

In some embodiments, the process 900 includes, at step/ operation 910, determining an object count. For example, the computing system 100 may determine a second object count corresponding to the distribution canister. For instance, the computing system 100 may receive, via one or more weighing operations, weight data for the distribution canister and determine the second object count based on the weight data and the intake identifier.

In some embodiments, the process 900 includes, at step/ operation 912, initiating a compliance operation. For example, the computing system 100 may initiate a compliance operation based on a comparison between the first object count and the second object count.

For example, the compliance operation may include one of (i) one or more verified operations initiated in response to the first object count matching the second object count or (ii) one or more error operations initiated in response to a deviation between the first object count and the second object count. The one or more error operations may include providing, via one or more user interfaces, a deviation alert indicative of the first object count, the second object count, the transitioning container, and/or the distribution canister.

In addition, or alternatively, in response to an order data object, the computing system 100 may control, via the robotic distribution device, a dispensation of one or more ordered objects of the plurality of transitioning objects from the distribution canister to a pouch container. The computing system 100 may modify the second object count based on a third object count identifying a number of the one or more ordered objects and, in some examples, the computing system 100 may generate a pouch data object including the intake identifier, the third object count, and/or an order identifier corresponding to the order data object.

VI. CONCLUSION

Many modifications and other embodiments will come to mind to one skilled in the art to which the present disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

VI. EXAMPLES

Example 1. A computer-implemented method, the computer-implemented method comprising receiving, by one or more processors, a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container; receiving, by the one or more processors, a canister identifier corresponding to a distribution canister; in response to receiving the transition identifier and the canister identifier, (i) assigning, by the one or more processors, the transition identifier and the intake identifier to a canister data object corresponding to the distribution canister, (ii) assigning, by the one or more processors, the canister identifier to a target intake data object corresponding to the intake identifier, and (iii) removing, by the one or more processors, the intake identifier and the transition identifier from a pallet data object corresponding to the pallet identifier; determining, by the one or more processors, a second object count corresponding to the distribution canister; and initiating, by the one or more processors, a compliance operation based on a comparison between the first object count and the second object count.

Example 2. The computer-implemented method of example 1, wherein receiving the transition identifier comprises receiving, via one or more scanning operations, scanned indicia data associated with the transitioning container; and identifying the transition identifier based on the scanned indicia data.

Example 3. The computer-implemented method of any of the preceding examples, wherein receiving the canister identifier comprises receiving, via one or more scanning operations, scanned indicia data associated with the distribution canister; and identifying the canister identifier based on the scanned indicia data.

Example 4. The computer-implemented method of any of the preceding examples, wherein the transition identifier and the canister identifier are received within a time threshold.

Example 5. The computer-implemented method of any of the preceding examples, wherein determining the second object count comprises receiving, via one or more weighing operations, weight data for the distribution canister; and determining the second object count based on the weight data and the intake identifier.

Example 6. The computer-implemented method of any of the preceding examples, wherein the first object count identifies a number of the plurality of transitioning objects within a subset of a plurality of intake objects corresponding to the intake identifier and the first object count is determined during one or more dispensing operations of the subset of the plurality of intake objects.

Example 7. The computer-implemented method of any of the preceding examples, wherein the compliance operation comprises one of (i) one or more verified operations initiated in response to the first object count matching the second object count or (ii) one or more error operations initiated in response to a deviation between the first object count and the second object count.

Example 8. The computer-implemented method of example 7, wherein the one or more error operations comprise providing, via one or more user interfaces, a deviation alert indicative of the first object count, the second object count, the transitioning container, or the distribution canister.

Example 9. The computer-implemented method of any of examples 7 through 8, wherein the one or more verified operations comprise in response to an order data object, controlling, via a robotic distribution device, a dispensation of one or more ordered objects of the plurality of transitioning objects from the distribution canister to a pouch container; modifying the second object count based on a third object count identifying a number of the one or more ordered objects; and generating a pouch data object comprising the intake identifier, the third object count, and an order identifier corresponding to the order data object.

Example 10. The computer-implemented method of any of the preceding examples, further comprising storing the intake identifier, the transition identifier, and the pallet identifier as a historic tuple.

Example 11. A computing system comprising memory and one or more processors communicatively coupled to the memory, the one or more processors configured to receive a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container; receive a canister identifier corresponding to a distribution canister; in response to receiving the transition identifier and the canister identifier, (i) assign the transition identifier and the intake identifier to a canister data object corresponding to the distribution canister, (ii) assign the canister identifier to a target intake data object corresponding to the intake identifier, and (iii) remove the intake identifier and the transition identifier from a pallet data object corresponding to the pallet identifier; determine a second object count corresponding to the distribution canister; and initiate a compliance operation based on a comparison between the first object count and the second object count.

Example 12. The computing system of example 11, wherein receiving the transition identifier comprises receiving, via one or more scanning operations, scanned indicia data associated with the transitioning container; and identifying the transition identifier based on the scanned indicia data.

Example 13. The computing system of any of examples 11 through 12, wherein receiving the canister identifier comprises receiving, via one or more scanning operations, scanned indicia data associated with the distribution canister; and identifying the canister identifier based on the scanned indicia data.

Example 14. The computing system of any of examples 11 through 13, wherein the transition identifier and the canister identifier are received within a time threshold.

Example 15. The computing system of any of examples 11 through 14, wherein determining the second object count comprises receiving, via one or more weighing operations, weight data for the distribution canister; and determining the second object count based on the weight data and the intake identifier.

Example 16. The computing system of any of examples 11 through 15, wherein the first object count identifies a number of the plurality of transitioning objects within a subset of a plurality of intake objects corresponding to the intake identifier and the first object count is determined during one or more dispensing operations of the subset of the plurality of intake objects.

Example 17. The computing system of any of examples 11 through 16, wherein the compliance operation comprises one of (i) one or more verified operations initiated in response to the first object count matching the second object count or (ii) one or more error operations initiated in response to a deviation between the first object count and the second object count.

Example 18. The computing system of example 17, wherein the one or more error operations comprise providing, via one or more user interfaces, a deviation alert indicative of the first object count, the second object count, the transitioning container, or the distribution canister.

Example 19. The computing system of any of examples 17 through 18, wherein the one or more verified operations comprise in response to an order data object, controlling, via a robotic distribution device, a dispensation of one or more ordered objects of the plurality of transitioning objects from the distribution canister to a pouch container; modifying the second object count based on a third object count identifying a number of the one or more ordered objects; and generating a pouch data object comprising the intake identifier, the third object count, and an order identifier corresponding to the order data object.

Example 20. One or more non-transitory computer-readable storage media including instructions that, when executed by one or more processors, cause the one or more processors to receive a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container; receive a canister identifier corresponding to a distribution canister; in response to receiving the transition identifier and the canister identifier, (i) assign the transition identifier and the intake identifier to a canister data object corresponding to the distribution canister, (ii) assign the canister identifier to a target intake data object corresponding to the intake identifier, and (iii) remove the intake identifier and the transition identifier from a pallet data object corresponding to the pallet identifier; determine a second object count corresponding to the distribution canister; and initiate a compliance operation based on a comparison between the first object count and the second object count.

The invention claimed is:

1. A computer-implemented method, the computer-implemented method comprising:

receiving, by one or more processors, a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container;

receiving, by the one or more processors, a canister identifier corresponding to a distribution canister;

in response to receiving the transition identifier and the canister identifier, (i) assigning, by the one or more processors, the transition identifier and the intake identifier to a canister data object corresponding to the distribution canister, (ii) assigning, by the one or more processors, the canister identifier to a target intake data object corresponding to the intake identifier, and (iii) removing, by the one or more processors, the intake identifier and the transition identifier from a pallet data object corresponding to the pallet identifier;

determining, by the one or more processors, a second object count corresponding to the distribution canister; and initiating, by the one or more processors, a compliance operation based on a comparison between the first object count and the second object count.

2. The computer-implemented method of claim 1, wherein receiving the transition identifier comprises:

receiving, via one or more scanning operations, scanned indicia data associated with the transitioning container; and identifying the transition identifier based on the scanned indicia data.

3. The computer-implemented method of claim 1, wherein receiving the canister identifier comprises:

receiving, via one or more scanning operations, scanned indicia data associated with the distribution canister; and identifying the canister identifier based on the scanned indicia data.

4. The computer-implemented method of claim 1, wherein the transition identifier and the canister identifier are received within a time threshold.

5. The computer-implemented method of claim 1, wherein determining the second object count comprises:

receiving, via one or more weighing operations, weight data for the distribution canister; and determining the second object count based on the weight data and the intake identifier.

6. The computer-implemented method of claim 1, wherein the first object count identifies a number of the plurality of transitioning objects within a subset of a plurality of intake objects corresponding to the intake identifier and the first object count is determined during one or more dispensing operations of the subset of the plurality of intake objects.

7. The computer-implemented method of claim 1, wherein the compliance operation comprises one of (i) one or more verified operations initiated in response to the first object count matching the second object count or (ii) one or more error operations initiated in response to a deviation between the first object count and the second object count.

8. The computer-implemented method of claim 7, wherein the one or more error operations comprise providing, via one or more user interfaces, a deviation alert indicative of the first object count, the second object count, the transitioning container, or the distribution canister.

9. The computer-implemented method of claim 7, wherein the one or more verified operations comprise:

in response to an order data object, controlling, via a robotic distribution device, a dispensation of one or more ordered objects of the plurality of transitioning objects from the distribution canister to a pouch container;

modifying the second object count based on a third object count identifying a number of the one or more ordered objects; and generating a pouch data object comprising the intake identifier, the third object count, and an order identifier corresponding to the order data object.

10. The computer-implemented method of claim 1, further comprising:

storing the intake identifier, the transition identifier, and the pallet identifier as a historic tuple.

11. A computing system comprising memory and one or more processors communicatively coupled to the memory, the one or more processors configured to:

receive a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container;

receive a canister identifier corresponding to a distribution canister;

in response to receiving the transition identifier and the canister identifier, (i) assign the transition identifier and the intake identifier to a canister data object corresponding to the distribution canister, (ii) assign the canister identifier to a target intake data object corresponding to the intake identifier, and (iii) remove the intake identifier and the transition identifier from a pallet data object corresponding to the pallet identifier;

determine a second object count corresponding to the distribution canister; and initiate a compliance operation based on a comparison between the first object count and the second object count.

12. The computing system of claim 11, wherein receiving the transition identifier comprises:

receiving, via one or more scanning operations, scanned indicia data associated with the transitioning container; and identifying the transition identifier based on the scanned indicia data.

13. The computing system of claim 11, wherein receiving the canister identifier comprises:

receiving, via one or more scanning operations, scanned indicia data associated with the distribution canister; and identifying the canister identifier based on the scanned indicia data.

14. The computing system of claim 11, wherein the transition identifier and the canister identifier are received within a time threshold.

15. The computing system of claim 11, wherein determining the second object count comprises:

receiving, via one or more weighing operations, weight data for the distribution canister; and determining the second object count based on the weight data and the intake identifier.

16. The computing system of claim 11, wherein the first object count identifies a number of the plurality of transitioning objects within a subset of a plurality of intake objects corresponding to the intake identifier and the first object count is determined during one or more dispensing operations of the subset of the plurality of intake objects.

17. The computing system of claim 11, wherein the compliance operation comprises one of (i) one or more verified operations initiated in response to the first object count matching the second object count or (ii) one or more error operations initiated in response to a deviation between the first object count and the second object count.

18. The computing system of claim 17, wherein the one or more error operations comprise providing, via one or more user interfaces, a deviation alert indicative of the first object count, the second object count, the transitioning container, or the distribution canister.

19. The computing system of claim 17, wherein the one or more verified operations comprise:

in response to an order data object, controlling, via a robotic distribution device, a dispensation of one or more ordered objects of the plurality of transitioning objects from the distribution canister to a pouch container;

modifying the second object count based on a third object count identifying a number of the one or more ordered objects; and generating a pouch data object comprising the intake identifier, the third object count, and an order identifier corresponding to the order data object.

20. One or more non-transitory computer-readable storage media including instructions that, when executed by one or more processors, cause the one or more processors to:

receive a transition identifier corresponding to a transitioning data object that comprises (a) a first object count of a plurality of transitioning objects within a transitioning container, (b) an intake identifier corresponding to the plurality of transitioning objects, and (c) a pallet identifier for a conveyor pallet configured to move the transitioning container;

receive a canister identifier corresponding to a distribution canister;

in response to receiving the transition identifier and the canister identifier, (i) assign the transition identifier and the intake identifier to a canister data object corresponding to the distribution canister, (ii) assign the canister identifier to a target intake data object corresponding to the intake identifier, and (iii) remove the intake identifier and the transition identifier from a pallet data object corresponding to the pallet identifier;

determine a second object count corresponding to the distribution canister; and initiate a compliance operation based on a comparison between the first object count and the second object count.

* * * * *